United States Patent
Drouet et al.

(10) Patent No.: US 10,822,295 B2
(45) Date of Patent: Nov. 3, 2020

(54) MENAQUINOL COMPOSITIONS AND METHODS OF TREATMENT

(71) Applicant: Epizon Pharma, Inc., New York, NY (US)

(72) Inventors: Keith E. Drouet, San Diego, CA (US); James A. Tumlin, Suford, PA (US)

(73) Assignee: EPIZON PHARMA, INC., New York, NY (US)

( * ) Notice: Subject to any disclaimer, the term of this patent is extended or adjusted under 35 U.S.C. 154(b) by 0 days.

(21) Appl. No.: 16/563,099

(22) Filed: Sep. 6, 2019

(65) Prior Publication Data

US 2020/0079718 A1 Mar. 12, 2020

Related U.S. Application Data

(60) Provisional application No. 62/730,149, filed on Sep. 12, 2018.

(51) Int. Cl.
| | | |
|---|---|---|
| C07C 46/10 | (2006.01) | |
| C07C 37/00 | (2006.01) | |
| C07C 67/03 | (2006.01) | |
| C07C 39/225 | (2006.01) | |
| C07C 50/14 | (2006.01) | |
| C07C 69/017 | (2006.01) | |
| A61P 1/16 | (2006.01) | |
| C07D 405/06 | (2006.01) | |

(52) U.S. Cl.
CPC ............ *C07C 46/10* (2013.01); *A61P 1/16* (2018.01); *C07C 37/00* (2013.01); *C07C 67/03* (2013.01); *C07D 405/06* (2013.01); *C07B 2200/13* (2013.01); *C07C 39/225* (2013.01); *C07C 50/14* (2013.01); *C07C 69/017* (2013.01)

(58) Field of Classification Search
CPC ......... C07C 46/10; C07C 37/00; C07C 67/03; C07C 37/002; C07C 46/00; A61P 1/16; C07D 405/06; C07B 2200/13
See application file for complete search history.

(56) References Cited

U.S. PATENT DOCUMENTS

| | | |
|---|---|---|
| 9,012,693 B2 | 4/2015 | Skattebol et al. |
| 9,464,021 B2 | 10/2016 | Mehta et al. |
| 9,512,153 B2 | 12/2016 | Moller et al. |
| 10,159,687 B2 | 12/2018 | Moller et al. |
| 10,688,064 B2 * | 6/2020 | Tumlin ............ A61K 9/0053 |
| 2011/0207967 A1 | 8/2011 | Skattebol et al. |
| 2015/0031651 A1 | 1/2015 | Moller et al. |
| 2016/0184254 A1 | 6/2016 | Aukrust et al. |
| 2018/0066326 A1 | 3/2018 | Bianchi et al. |
| 2018/0199610 A1 | 7/2018 | Vermeer |

FOREIGN PATENT DOCUMENTS

| | | | |
|---|---|---|---|
| WO | WO2007/095630 | 8/2007 | |
| WO | WO2013/128037 | 9/2013 | |
| WO | WO2013128037 | 9/2013 | |
| WO | WO-2016151447 A1 * | 9/2016 | ............... C12P 7/66 |
| WO | WO2019194690 | 10/2019 | |

OTHER PUBLICATIONS

C. Boullais et al, A Short and Convenient Synthesis of [1-18O] and [4-18O] Vitamin K1, Journal of Labelled Compounds and Radiopharma. vol. XLI, No. 2, 1997; John Wiley & Sons.
M. Halder et al., Vitamin K Double Bonds beyond Coagulation Insights into Differences between Vitamin K1 and K2 in Health and Disease, International Journal of Molecular Sciences; Feb. 19, 2019, 20, 896.
S. U. Nigwekar et al., A Nationally Representative Study of Calcilic Uremic Arteriolopathy Risk Factors, J AmSoc Nephrol 27: 1-9, 2016.
J. Himmelfarb et al., Plasma protein thiol oxidation and carbonyl formation in chronic renal failure, Kidney International, vol. 58 (2000), pp. 2571-2578.
T. Sato et al., Comparison of menaquinone-4 and menaquinone-7 bioavailability in healthy women, Nutrition Journal, 2012, 11:93.
S. U. Nigwekar et al., Vitamin K—Dependent Carboxylation of Matrix Gla Protein Influences the Risk of Calciphylaxis, J Am Soc Nephrol, 2017, 28: 1717-1722.
S. U. Nigwekar et al., Nutritional Vitamin D Supplementation in Dialysis: A Randomized Trial, Clin J Am Soc Nephrol, 2015,10: 611-619.
J. D. Morrow et al., A series of prostaglandin F2-like compounds are produced in vivo in humans by . . . , Proc. Natl. Acad. Sci. USA, 1990, vol. 87, pp. 9383-9387.
T. Miyata et al, Increased carbonyl modification by lipids and carbohydrates in diabetic nephropathy, Kidney International, 1999, vol. 56, Suppl. 71, pp. S-54-S-56.

* cited by examiner

*Primary Examiner* — Paul A Zucker
(74) *Attorney, Agent, or Firm* — Sam L. Nguyen; HDC IP Law, LLP

(57) ABSTRACT

The present application discloses methods for the efficient preparation of high purity compounds of the Formula I, and their methods of use.

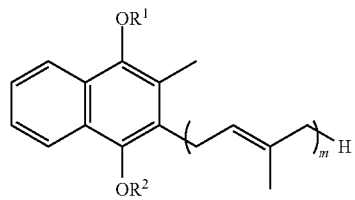

Also disclosed herein are pharmaceutical compositions comprising a therapeutically effective amount of a menaquinol compound as disclosed above, or a mixture thereof, and a pharmaceutically acceptable excipient, wherein the composition is effective for the treatment of a condition associated with vitamin K selected from for the treatment of osteoporosis and arteriosclerosis.

7 Claims, 3 Drawing Sheets

Uremia and Dialysis Induced Oxidation of KH2 Reduces Functional Carboxylation of Vitamin K Dependent Proteins

Figure-1  R ~

Fig. 3. In vivo plasma protein carbonyl formation. *$P < 0.05$ vs. normal volunteers ($N = 10$ in each group).

MENAQUINOL COMPOSITIONS AND METHODS OF TREATMENT

RELATED APPLICATION

This application claims the benefit of U.S. Provisional Application No. 62/730,149 filed on Sep. 12, 2018.

FIELD OF INVENTION

The present invention relates to compounds, compositions and formulations, and combinations thereof, for the treatment of diseases associated with vitamin K, its reduced and bioactive form menaquinol, including osteoporosis and osteopenia.

BACKGROUND OF THE INVENTION

Vitamin K is known as a group of structurally similar, fat-soluble vitamins. Vitamin $K_2$ or menaquinone has nine related compounds that can be subdivided into the short-chain menaquinones (such as menaquinone-4 or MK-4) and the long-chain menaquinones, such as MK-7, MK-8 and MK-9-12. The vitamins include phylloquinone (K1), menaquinones (K2) and menadione (K3). Plants synthesize vitamin K1 while bacteria can produce a range of vitamin K2 forms, including the conversion of K1 to K2 by bacteria in the small intestines. Vitamin K3 is synthetic version of the vitamin, and due to its toxicity, has been banned in by the US Food and Drug Administration for human uses.

It has been established that taking broad-spectrum antibiotics can reduce vitamin K production in the gut by nearly 74% in people compared to those not taking these antibiotics. Diets that are low in vitamin K also decrease the body's vitamin K concentration. Vitamin K1 is preferentially used by the liver as a clotting factor. Vitamin K2 is used preferentially in the brain, vasculature, breasts and kidneys. Vitamin K2 contributes to production of myelin and sphingolipids (fats essential for brain health) and protects against oxidative damage in the brain. Vitamin K2, such as MK-4, promotes bone health by stimulating connective tissue production in bone.

Vitamin K2, which is the main storage form in animals, has several subtypes, which differ in chain length of the isoprenoid group or residue in the side chains. These vitamin K2 homologues are called menaquinones, and are characterized by the number of isoprenoid residues in their side chains. For example, MK-4 has four isoprene residues in its side chain, and is the most common type of vitamin K2 in animal products. MK-4 is normally synthesized from vitamin $K_1$ in certain animal tissues (arterial walls, pancreas and testes) by replacement of the phytyl group with an unsaturated geranyl group containing four isoprene units. Unlike MK-4, MK-7 is not produced by human tissue. MK-7 may be converted from phylloquinone ($K_1$) in the colon by *E. coli* bacteria. MK-4 and MK-7 are sold in the U.S. in dietary supplements for bone health. MK-4 has been shown to decrease the incidence of fractures. MK-4, at a dose of 45 mg daily, has been approved by the Ministry of Health in Japan since 1995 for the prevention and treatment of osteoporosis.

Osteoporosis is a disease of bone that leads to an increased risk of fracture. In osteoporosis the bone mineral density (BMD) is reduced, bone micro architecture is disrupted, and the amount and variety of non-collagenous proteins in bone is altered. The World Health Organization define osteoporosis (in women) as a bone mineral density 2.5 standard deviations below peak bone mass, that is, for an average 30-year-old healthy female. Osteoporosis is most common in women after menopause (referred to as post-menopausal osteoporosis). Osteoporosis may also develop in men, and may occur in anyone in the presence of particular hormonal disorders and other chronic diseases or as a result of medications, specifically glucocorticoids, when the disease is called steroid- or glucocorticoid-induced osteoporosis and as a result of nutritional deficiency states or other metabolic disorders, for example, hyponatremia or as a secondary consequence of cancer.

Osteopenia is a condition where bone mineral density is lower than normal. It is considered by many doctors to be a precursor to osteoporosis. Specifically, osteopenia is defined as a bone mineral density T score between −1.0 and −2.5. Osteopenia can be induced under specific conditions such as long-term bed rest.

The underlying mechanism in most cases of osteoporosis is an imbalance between bone resorption and bone formation. In normal bone, there is constant matrix remodelling of bone. It has been established that up to 10% of all bone mass may be undergoing remodelling at any point in time. Bone is resorbed by osteoclast cells, which are derived from bone marrow precursor cells. In the remodelling process new bone is deposited by osteoblast cells. The three main mechanisms by which osteoporosis develops include an inadequate peak bone mass (the skeleton develops insufficient mass and strength during growth), excessive bone resorption and inadequate formation of new bone during remodelling. Hormonal factors strongly determine the rate of bone resorption; lack of estrogen (e.g. as a result of menopause) increases bone resorption as well as decreasing the deposition of new bone that normally takes place in weight-bearing bones. In addition to estrogen, calcium metabolism plays a significant role in bone turnover, and deficiency of calcium and vitamin D leads to impaired bone deposition; in addition, the parathyroid glands react to low calcium levels by secreting parathyroid hormone, which increases bone resorption to ensure sufficient calcium in the blood. Medications used for the treatment of osteoporosis includes calcium, vitamin D, vitamin K, bisphosphonates, Calcitonin, Teriparatide, strontium ranelate, hormone replacement and selective estrogen receptor modulators.

It has been established that cardiovascular disease (CVD) is the most frequent cause of death in patients with chronic kidney disease (CKD). When compared to the general population, the cause of death attributed to CVD is about 10-20 times higher in CKD patients when they are being treated with hemodialysis. In addition, it has been demonstrated that vascular calcification and the correlated arterial stiffness is prevalent in the incidence of CVD. In addition, patient with CKD undergoing dialysis treatment have a 3 times higher risk of bone fractures, such as vertebral fractures and other type of bone fractures.

Vitamin K, including MK-7, are present in low concentrations in a typical diet. It has also been established that there exists a direct correlation between the level of vitamin K in a patient's blood and the incidence of vascular calcification, bone density and bone strength. Accordingly, the supplemental use of vitamin K, such as MK-7 and its also fat-soluble hydroquinone (menaquinol) derivatives as disclosed herein, may provide significant clinical benefit for reducing vascular calcification noted, in part, by arterial stiffness, and increase bone mineralization or increase in bone mineral density, that will help treat or prevent CVD, and treat or prevent bone diseases in patients with CKD. In one aspect, the disclosed method for the administration of MK-7 and its fat-soluble hydroquinone derivatives, or combinations thereof, may be used in the treatment or reduction of vascular calcification, increase in bone mineral density and for the treatment, reduction or prevention of bone diseases, such as in patients with CKD.

It has also been established that in food products, vitamin K1 is bound to the chloroplast membrane of leafy green vegetables. MK-4, which is derived from the conversion of menadione, a synthetic analog of vitamin K, is found in animal products such as eggs and meats. Long chain menaquinones such as MK-7, MK-8 and MK-9, are found in fermented foods such as cheese, curd and sauerkraut. It has also been established that the effects of long chain MK-n such as MK-7 on normal blood coagulation is greater and longer lasting than vitamin K1 and MK-4. MK-7 has also been shown to have a long half-life in serum when compared to MK-4, providing a better carboxylation-grade of osteocalcin compared to Vitamin K1. See Sato et al., Nutrition Journal, 2012, 11:93.

Nutritional doses of MK-7 can be established to be well absorbed in humans, and as a consequence, provide a significant increase in the serum for MK-7 levels. However, very little information is known of MK-7, and menaquinol-7, primarily because MK-7 and menaquinol-7, are not readily available nor commercially accessible via standard synthetic methods.

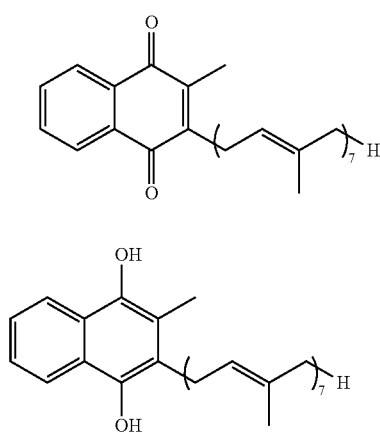

MK-7

Menaquinol-7

In one embodiment, the present application discloses a novel and efficient method for the preparation of menaquinol-7 and its hydroquinone derivatives. The novel method uses a nickel(0)-catalyzed coupling reaction and uses readily available starting materials, and provides menaquinol-7 and its hydroquinone derivatives in high yields and high chemical purity.

The foregoing examples of the related art and limitations are intended to be illustrative and not exclusive. Other limitations of the related art will become apparent to those of skill in the art upon a reading of the specification and a study of the drawings or figures as provided herein.

SUMMARY OF THE INVENTION

Therefore, a continuing need exists for formulations that are effective for these indications. The following embodiments, aspects and variations thereof are exemplary and illustrative are not intended to be limiting in scope.

In one aspect, there is provided a chemoselective method for preparing a menaquinol compound with high regioselectivity, high isomeric purity and high chemical purity, the method comprising:

(a) contacting a compound of the Formula III:

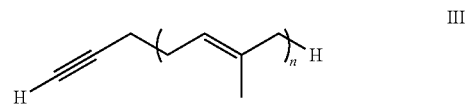

III where n is 6, 7, 8 or 9;

with a trialkylaluminum compound of the formula $R_3Al$, together with a Zr catalyst, in an aprotic solvent to form a mixture of compounds of the Formulae IVa and IVb:

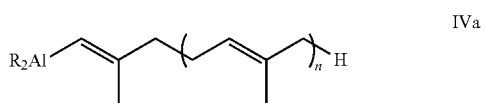

IVa

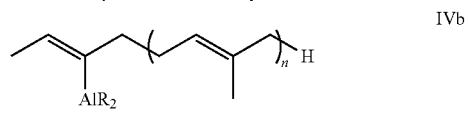

IVb wherein R is selected from the group consisting of $CH_3$— and $CH_3CH_2$—;

(b) contacting the intermediate compound of the Formulae IVa and IVb with a chloromethylquinone of the Formula V and a transition metal catalyst:

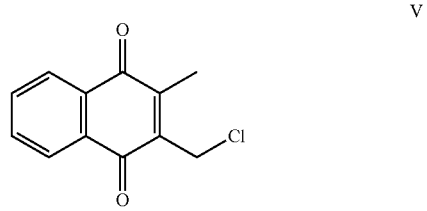

V to provide a mixture comprising a compound of the Formulae VIa and the regioisomer VIb:

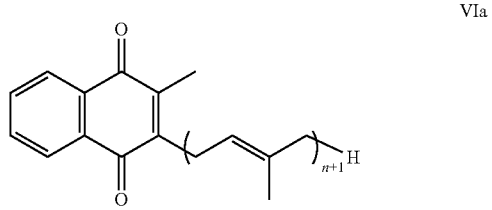

VIa

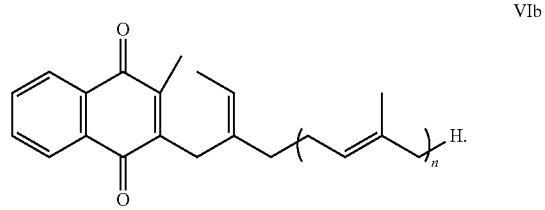

VIb

In one variation of the trialkylaluminum compound of the formula $R_3Al$, R is —$CH_3$. In one aspect, the method further comprises crystallizing the mixture of the Formulae VIa and VIb using a solvent mixture to form a mixture of the compound of the Formula VIa and VIb, wherein the ratio of VIa to VIb is greater than 99.8:0.2, and the purity of VIa is greater than 99.6% as determined by HPLC. In another aspect of the above method, the purity of VIa is greater than 99.8% as determined by HPLC. The level of purity of the products achieved using the present synthesis provides pharmaceutical grade compositions that are greater that those products obtained by fermentation processes.

In one variation of the method in step (b), the unreacted or excess trialkylaluminum compound and the aprotic solvent in the reaction are not removed from the reaction mixture before contacting the intermediate compound with a compound of Formula V. On a large scale process, the elimination of this processing step reduces the potentially hazardous handling of the pyrophoric compound. In one variation, the trialkylaluminum compound is $Me_3Al$ or $Al_2Me_6$. In one variation, the zirconium catalyst is an organozirconium catalyst. In another variation, the organozirconium catalyst is selected from the group consisting of zirconocene dichloride ($Cp_2ZrCl_2$), rac-(ebi)$ZrCl_2$ and rac-(ebthi)$ZrCl_2$. In another variation, the metal catalyst is $(Ph_3P)_2Ni(0)$, or $(Ph_3P)_2Pd(0)$, that may be prepared from the addition of $NiCl_2$ or $PdCl_2$ (or other Ni(II) and Pd(II) salt precursors) to 2 $PPh_3$ followed by addition of 2 equivalents of n-BuLi in an aprotic solvent such as THF. In another variation, the zirconium catalyst is added as a solution in an aprotic solvent such as toluene, $CF_3Ph$, DCM or 1,2-dichloroethane.

In another aspect of the method, the metal catalyst is a nickel(0) catalyst. In another aspect, the nickel(0) catalyst is $(Ph_3P)_2Ni(0)$. In another aspect, more than 1 molar equivalent to 1.4 molar equivalents of the trialkylaluminum compound is added relative to the compound of the Formula III. In one variation, 1.2 to 1.4 molar equivalents of the trialkylaluminum compound is added relative to the compound of the Formula III. In another variation, about 1.2 molar equivalents of the trialkylaluminum compound is added relative to the compound of the Formula III.

In another aspect of the above method, the solvent mixture for crystallization of the compound of the Formulae VIa comprises ethyl acetate and a $C_1$-$C_3$ alcohol. In one variation, the $C_1$-$C_3$ alcohol is selected from methanol, ethanol, propanol and isopropanol. In another variation, the EtOAc: $C_1$-$C_3$ alcohol is from about 1:5 to about 2:5. In another variation, the solvent mixture is EtOAc:EtOH at a ratio of 1:5. In another variation, the solvent mixture comprises of about 15-20% EtOAc in EtOH, 20-25% EtOAc in EtOH, or about 20-22% EtOAc in EtOH. In another variation, the solvent mixture comprises of about 25-30% EtOAc in EtOH.

In another embodiment, there is provided a pharmaceutically pure menaquinone compound of the Formula VIa:

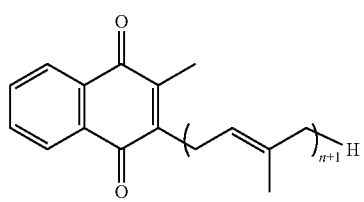

VIa wherein n is 6, 7, 8, or 9; and wherein the regioisomer of VIa is greater that 99.8% as measured by HPLC, and the chemical purity of VIa is greater than 99.6% as measured by HPLC. In one variation of the compound VIa, n is 7, and the regioisomer of VIa is greater that 99.8% by HPLC, and the chemical purity of VIa is greater than 99.6% as measured by HPLC. In another aspect of the above compound, the pharmaceutically pure menaquinone compound where n is 6.

In one variation, there is provided a pharmaceutically pure compound of the Formula VIa prepared by the method as disclosed above, wherein n is 6, 7, 8 or 9; and wherein the regioisomer of VIa is greater that 99.8% as measured by HPLC, and the purity is greater than 99.6% as measured by HPLC.

In another aspect, the method further comprises contacting the compound of the Formula VIa with a metal or other reducing agent and an acid or other source of protons for a sufficient period of time under conditions to form a menaquinol compound of the Formula VII:

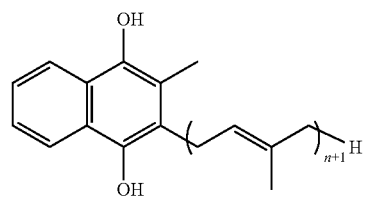

VII wherein n is 6, 7, 8 or 9.

In one variation, the metal is Zn, $SnCl_2$, $FeCl_3$, $FeCl_3.3H_2O$ and $FeCl_3.6H_2O$ and the acid is acetic acid or hydrochloric acid. In another variation, the reduction may be performed with N,N-diethylhydroxylamine (DEH) in HCl, such as dilute HCl. In another variation, the reduction may be performed with $FeCl_3$ or $FeCl_3.3H_2O$ and an acid such as HCl. In one variation of the method, the reduced product may be isolated or purified, or the reduced product may be further acylated in situ, without any further isolation or purification.

In another aspect of the method, the compound of the Formula VII is acylated with an acylating agent, for purposes of stabilization and isolation, selected from the group consisting of:

a) an acid halide selected from the group consisting of Formulae 15.a, 16.a, 17.a, 18.a, 20.a, 21.a, 22.a, 23, 24.a, 25.a, 26.a, 27.a and 28.a, wherein X is —Cl, —Br, —I, as well as any of several other known leaving groups in the art (e.g., imidazolyl, —$SO_2R$ and —$SO_2Ar$, etc. where Ar is phenyl, toluyl and substituted phenyl and R is methyl, ethyl, phenyl and substituted phenyl) and a base selected from the group consisting of $Cs_2CO_3$, $CsHCO_3$, CsOH, $LiCO_3$, $Na_2CO_3$, $K_2CO_3$, $KHCO_3$, NaOAc, $NaHCO_3$, or other organic bases (e.g., $Et_3N$, DABCO, DBU, DBN, etc.); or b) an acid anhydride selected from the group consisting of Formulae 15.a, 16.a, 17a, 18.a, 20.a, 21.a, 22.a, 23, 24.a, 25.a, 26.a, 27.a and 28.a, wherein X is —OC(O)R' wherein R' is —$C_{1-6}$alkyl and Zn, or a base selected from the group consisting of $Cs_2CO_3$, $CsHCO_3$, CsOH, $LiCO_3$, $Na_2CO_3$, $K_2CO_3$, $KHCO_3$, NaOAc and $NaHCO_3$;

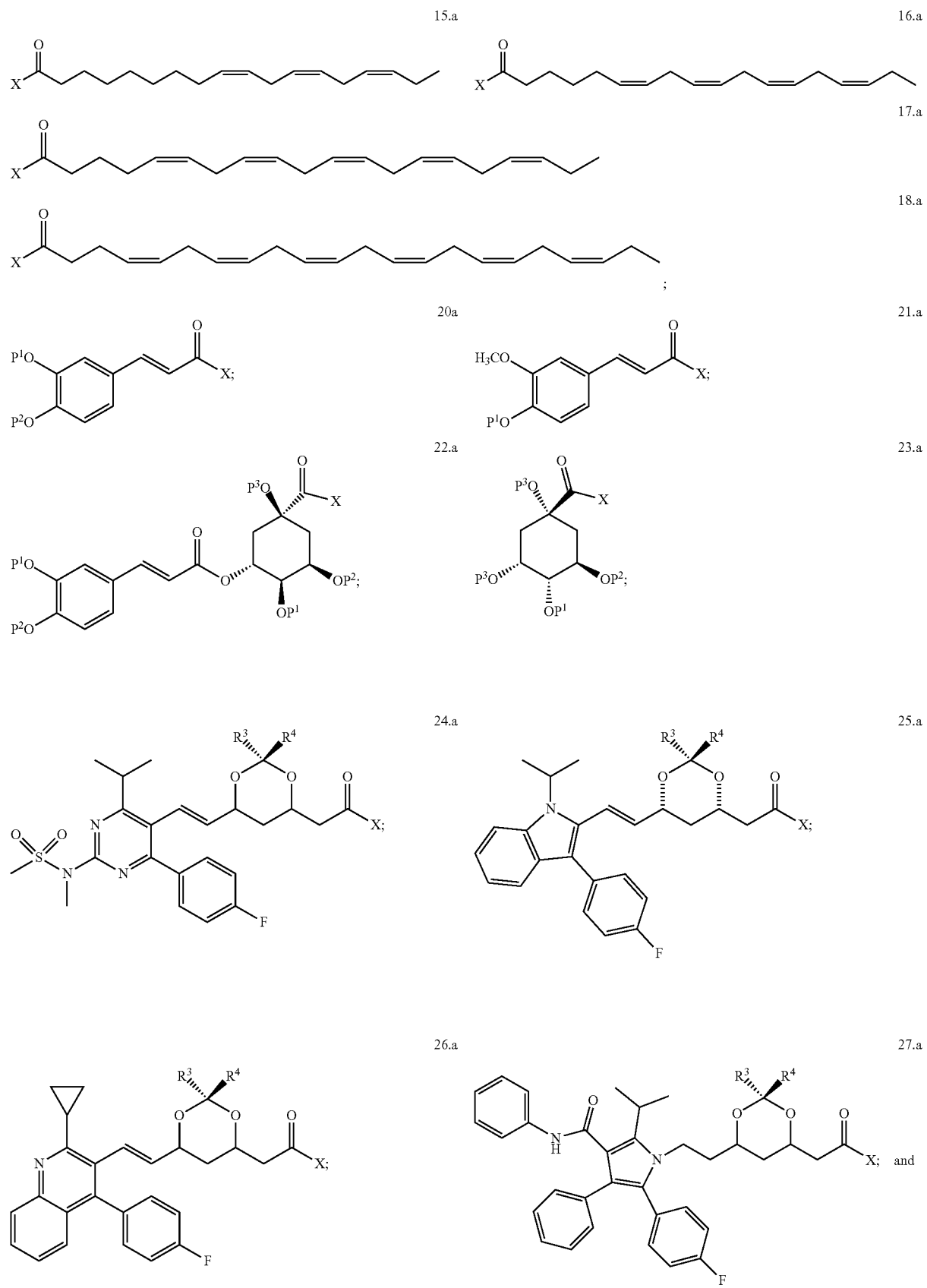

-continued

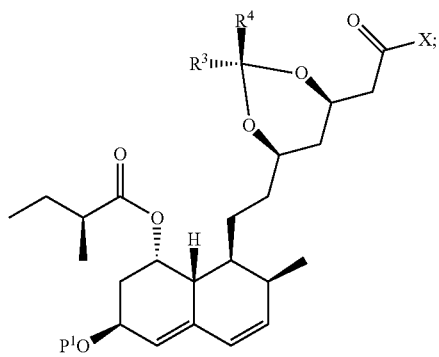

28.a wherein: $P^1$ and $P^2$ are each independently a protecting group selected from the group consisting of —$CH_2C_6H_5$, -THP (tetrahydropyranyl) or $P^1$ and $P^2$ together with the oxygen to which they are attached form a cyclic acetonide, benzyl acetal, or p-methoxybenzyl acetal;

$P^3$ is a hydroxyl protecting group selected from the group consisting of -THP, acetyl, benzoyl, β-methoxyethoxymethyl ether (MEM), dimethoxytrityl, methoxymethyl ether (MOM), p-methoxybenzyl ether (PMB), methylthiomethyl ether, pivaloyl (Piv) and trityl (Tr); and each $R^3$ and $R^4$ is independently H, —$CH_3$, —$CH_2CH_3$ and —$CH_2C_6H_5$;

to form a menaquinol compound of the Formula I

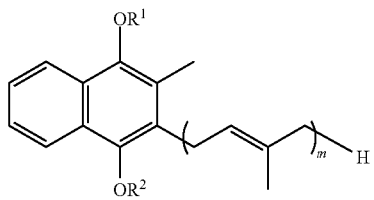

I wherein:
m is 7, 8, 9 or 10; and
each $R^1$ and $R^2$ is independently H or selected from the group consisting of:

15

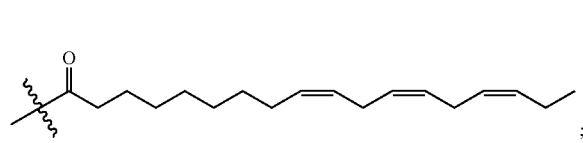

16

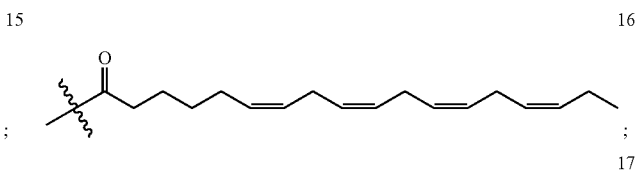

17

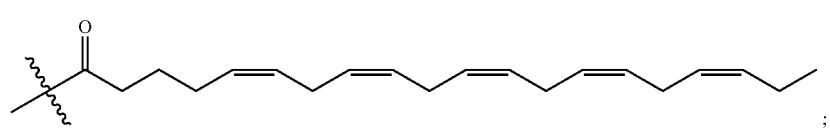

18

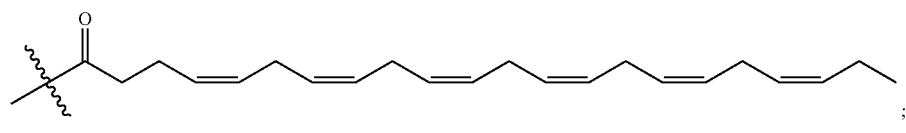

20

21

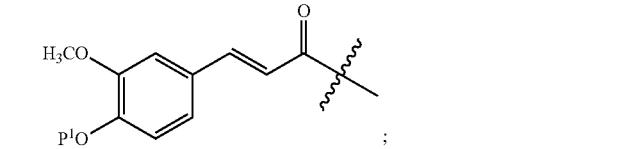

22

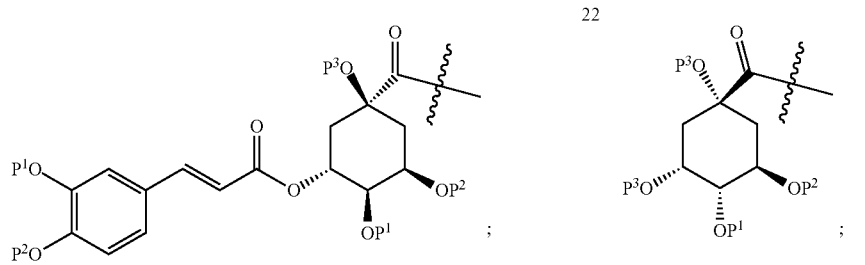

23

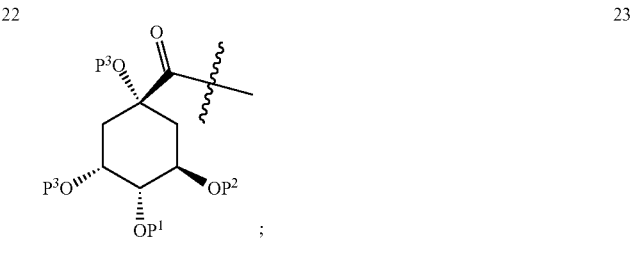

-continued

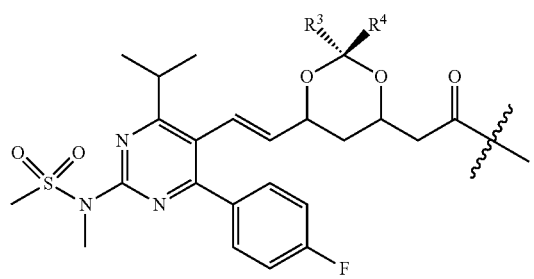

24

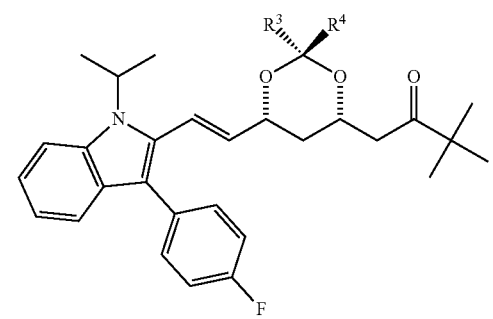

25

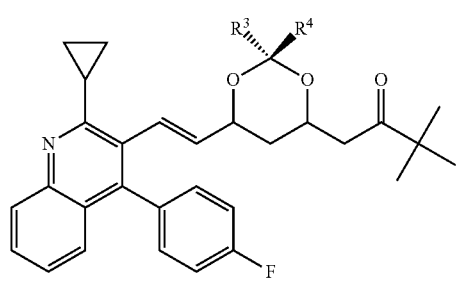

26

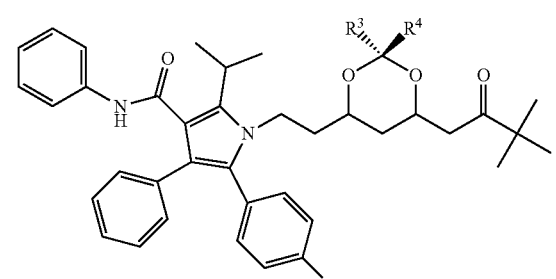

27

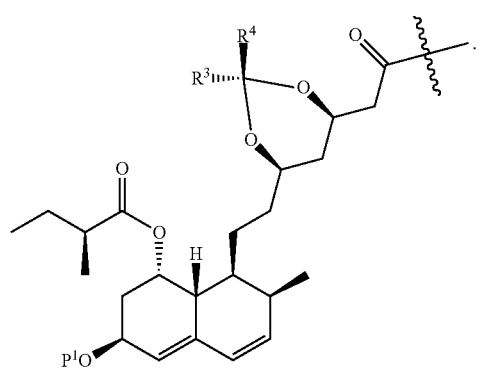

28

In one variation, the compound of the Formula VII is prepared and acylated in situ with the acylating agent. In another variation, the acylated products are the ester derivatives of statin compounds such as rosuvastatitn, pitavastatin, atorvastatin, or esters derived from omega-3 fatty acids such as alpha-linolenic acid, stearidonic acid, eicosapentaenoic acid and dodecahexenoic acid, or esters derived from acids found in coffee, such as caffeic acid, ferulic acid, chlorogenic acid and quinic acid, as their hydroxyl protected derivatives. In one variation, R' is —CH$_3$ or —CH$_2$CH$_3$, isopropyl or t-butyl. In another variation of the acylation reaction, the acylation may be performed in a solvent selected from the group consisting of ethyl acetate, THF, toluene, diethyl ether, dichloromethane or acetonitrile.

In another aspect, the method comprises further removing the hydroxyl protecting group $R^1$, $R^2$, $R^3$, $R^4$, $P^1$, $P^2$ and $P^3$. The removal of the protecting group such as —CH$_2$C$_6$H$_5$ may be performed, for example, by hydrogenation with hydrogen in Pd/C. Protecting groups such as -THP (tetrahydropyranyl), acetyl, benzoyl, β-methoxyethoxymethyl ether (MEM), dimethoxytrityl, methoxymethyl ether (MOM), p-methoxybenzyl ether (PMB), methylthiomethyl ether, pivaloyl (Piv) and trityl (Tr); a cyclic acetonide, acetals, ketals such as benzyl acetal or p-methoxy-benzyl acetal may be removed by acid hydrolysis. Standard methods for the preparation, formation and removal of hydroxyl protecting groups may be found, for example in T.W. Greene, Protecting Groups in Organic Synthesis, 3rd edition, John Wiley & Sons, Inc. 1999.

In another embodiment, the application provides a menaquinol compound of the Formula I:

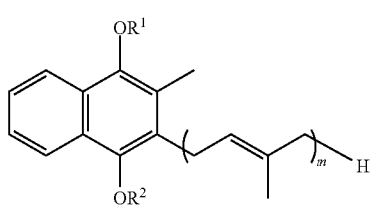

I wherein:

m is 7, 8, 9 or 10;

each of $R^1$ and $R^2$ is independently H or is independently selected from the group consisting of:

15
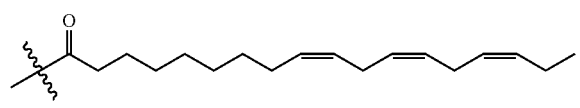
16
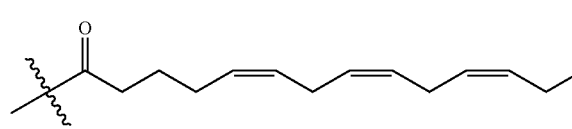
17
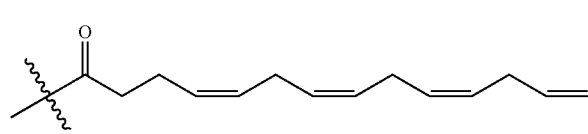
18
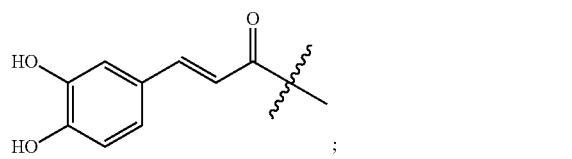
20
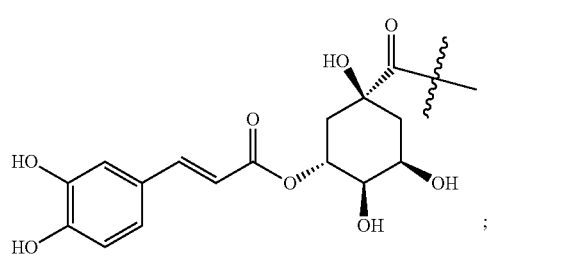
21
22
23
24
25
26
27
; and -continued

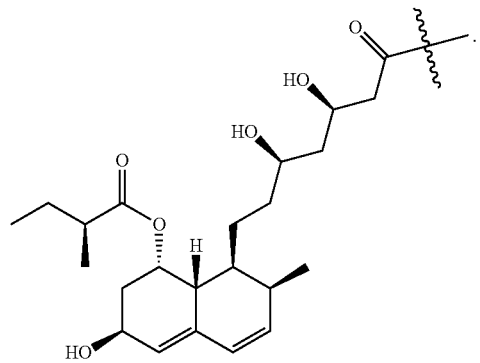

In another aspect, the application discloses the compounds of the Formula I, wherein:
$R^1$ and $R^2$ are both the residue 15;
$R^1$ and $R^2$ are both the residue 16;
$R^1$ and $R^2$ are both the residue 17;
$R^1$ and $R^2$ are both the residue 18;
$R^1$ and $R^2$ are both the residue 20;
$R^1$ and $R^2$ are both the residue 21;
$R^1$ and $R^2$ are both the residue 22;
$R^1$ and $R^2$ are both the residue 23;
$R^1$ and $R^2$ are both the residue 24;
$R^1$ and $R^2$ are both the residue 25;
$R^1$ and $R^2$ are both the residue 26;
$R^1$ and $R^2$ are both the residue 27; and $R^1$ and $R^2$ are both the residue 28.

In another aspect, the application discloses the compounds of the Formula I, wherein:
$R^1$ is H and $R^2$ is the residue 15; $R^2$ is H and $R^1$ is the residue 15;
$R^1$ is H and $R^2$ is the residue 16; $R^2$ is H and $R^1$ is the residue 16;
$R^1$ is H and $R^2$ is the residue 17; $R^2$ is H and $R^1$ is the residue 17;
$R^1$ is H and $R^2$ is the residue 18; $R^2$ is H and $R^1$ is the residue 18;
$R^1$ is H and $R^2$ is the residue 20; $R^2$ is H and $R^1$ is the residue 20;
$R^1$ is H and $R^2$ is the residue 21; $R^2$ is H and $R^1$ is the residue 21;
$R^1$ is H and $R^2$ is the residue 22; $R^2$ is H and $R^1$ is the residue 22;
$R^1$ is H and $R^2$ is the residue 2; $R^2$ is H and $R^1$ is the residue 2;
$R^1$ is H and $R^2$ is the residue 24; $R^2$ is H and $R^1$ is the residue 24;
$R^1$ is H and $R^2$ is the residue 25; $R^2$ is H and $R^1$ is the residue 25;
$R^1$ is H and $R^2$ is the residue 26; $R^2$ is H and $R^1$ is the residue 26;
$R^1$ is H and $R^2$ is the residue 27; $R^2$ is H and $R^1$ is the residue 27; and
$R^1$ is H and $R^2$ is the residue 28; $R^2$ is H and $R^1$ is the residue 28.

In another embodiment, there is provided a compound of the Formula I:

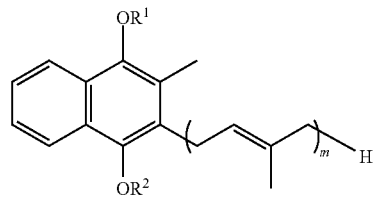

wherein: m is 7, 8, 9 or 10;
each of $R^1$ and $R^2$ is independently H or is independently selected from the group consisting of:

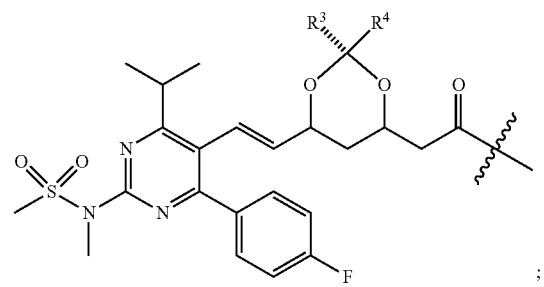

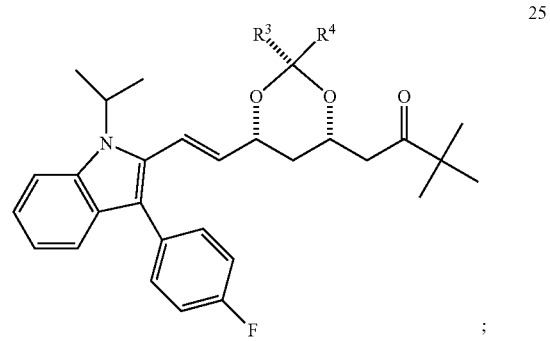

-continued

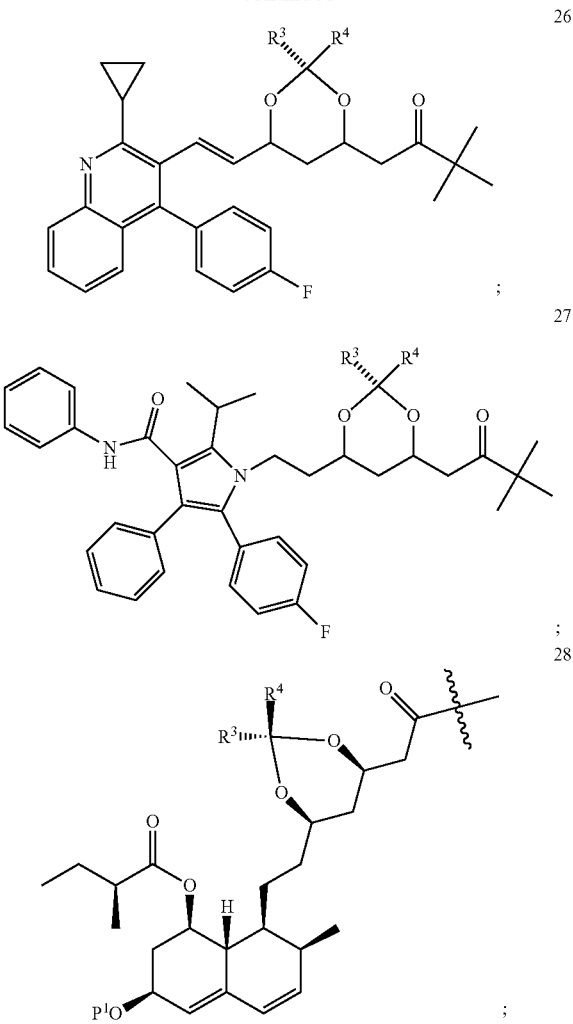

wherein each $R^3$ and $R^4$ is independently H, —$CH_3$, —$CH_2CH_3$ and —$CH_2C_6H_5$.

In one variation of the above compound, $R^3$ and $R^4$ are both —$CH_3$. In another variation, each $R^3$ and $R^4$ is independently H and —$CH_2C_6H_5$.

In another aspect of the disclosed method of treatment and method of prevention as recited herein, the compound is of the Formula III:

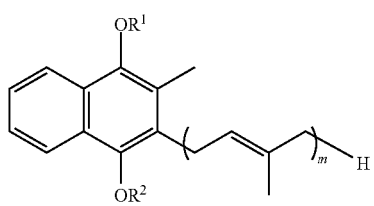

III wherein: m is 7, 8, 9 or 10; and each of $R^1$ and $R^2$ is independently H or is independently selected from the group consisting of —$C(O)C_{1-6}$alkyl. As used herein, the group $C_{1-6}$alkyl includes methyl, ethyl, propyl, iso-propyl, cyclopropyl, butyl, iso-butyl, pentyl, iso-pentyl, hexyl, cyclohexyl and 1-methylpentyl. In one variation, the compound is of the Formula IIIa, wherein m is 7 and both $R^1$ and $R^2$ are —$C(O)C_{1-6}$alkyl. In another variation, the compound is of the Formula IIIb, wherein m is 7 and both $R^1$ and $R^2$ are —$C(O)CH_3$.

In another aspect, the application discloses a pharmaceutical composition comprising a therapeutically effective amount of a menaquinol compound as disclosed above, or a mixture thereof, and a pharmaceutically acceptable excipient, wherein the composition is effective for the treatment of a condition associated with vitamin K selected from for the treatment of osteoporosis and arteriosclerosis.

In another aspect, the present application discloses a method for the treatment of a disease in a mammal selected from the group consisting of neurodegenerative diseases, retinopathy, rheumatoid polyarthritis, atherosclerosis, amyotrophic lateral sclerosis, cerebral ischemia, cataracts, systemic infections, pathologies associated with cutaneous aging and with senescence in tissues, pathologies associated with mitochondrial dysfunction, cachexia associated with under nutrition, wherein the treatment is associated with the increase in the longevity of mammals, the method comprises the administration of a therapeutically effective amount of a compound or composition comprising a menaquinol compound as disclosed above, or a mixture thereof.

In another embodiment, there is provided a method for treating a mammal with a disease selected from the group consisting of vitamin K deficiency, osteoporosis, a proliferative disease, and a cardiovascular disease, comprising administering to the mammal a therapeutically effective amount of a compound as disclosed herein, or a mixture thereof. In another aspect of the method, the proliferative disease is selected from the group consisting of cancer, leukemia and an inflammatory disease.

In another embodiment, there is provided a method for the treatment or prevention of osteoporosis and/or osteopenia, the method comprising administering to a patient in need of treatment, a therapeutically effective amount of a composition comprising a compound as disclosed above, or a mixture thereof.

In another embodiment, there is provided a method of treating, preventing, slowing the progression of, arresting, and/or reversing calciphylaxis in a mammal in need thereof, the method comprising administering to the mammal a therapeutically effective amount of a composition comprising substantially pure menaquinol compound as disclosed herein, and a pharmaceutically acceptable excipient, to prevent, slow the progression of, arrest, or reverse calciphylaxis. In one aspect of the method, the mammal has distal calciphylaxis and/or central calciphylaxis. In another aspect, the mammal has diabetes, chronic kidney disease or end stage renal disease. In another aspect, the mammal has stage 3, stage 4 or stage 5 chronic kidney disease. In another aspect of the method, the mammal is undergoing hemodialysis. In yet another aspect, the mammal is receiving non-warfarin-based anti-coagulant therapy.

In another aspect of the above method, the anti-coagulant therapy is oral anti-coagulation therapy. In another aspect, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban. In another aspect, the mammal has chronic obstructive pulmonary disease (COPD). In another aspect, the mammal has a calciphylaxis-related dermal lesion. In another aspect of the method, administration of the composition reduces the total surface area of the dermal lesion by at least 10%, 20%, 30%, 40%, 50%, 60%, 70%, 80%, 90% or 100%. In another aspect of the method, administration of the substantially pure compound as disclosed herein, to the mammal increases the mammal's serum T50 value by at least 10%, 20%, 30%, 40%, 50%, 60%, 70%, 80%, 90% or 100%) relative to the mammal's serum T50 value prior to administration of the disclosed compound. In another aspect, administration of the disclosed compound increases a ratio of a carboxylated to a non-carboxylated of a Vitamin K dependent protein in plasma of the mammal after administration of the composition is greater than prior to administration of the composition. In one aspect of the method, the increase of the ratio of a carboxylated to a non-carboxylated of a Vitamin K dependent protein in plasma of the mammal after administration of the composition is by at least 5%, 10%, 15%, 20%, 25%, 30%, 35%, 40%, 45% 50%, 55%, 60%, 65%, 70%, 75%, 80%, 85%, 90%, 95%, or 100% relative to the ratio prior to administration.

In certain embodiments of the above, the administration of the disclosed compounds decreases the amount of a non-carboxylated Vitamin K-dependent protein in the subject's plasma, for example, by at least 5%, 10%, 15%, 20%, 25%, 30%, 35%, 40%, 45% 50%, 55%, 60%, 65%, 70%, 75%, 80%, 85%, 90%, 95% or 100% relative to the amount prior to administration of the compounds. In certain variations, the Vitamin K-dependent protein is selected from Matrix Gla Protein (MGP), Growth Arrest Specific Gene 6 (Gas-6) protein, PIVKA-II protein, osteocalcin, activated Protein C, activated Protein S, factor II, factor VII, factor IX, and factor X.

In certain variation of the above methods, the administration of the compounds increases the plasma level of osteoprotegerin or Fetuin A, for example, by at least 5%, 10%, 15%, 20%, 25%, 30%, 35%, 40%, 45% 50%, 55%, 60%, 65%, 70%, 75%, 80%, 85%, 90%, 95%, or 100% relative to the plasma concentration of osteoprotegerin or Fetuin A prior to administration of the compounds. In other variations, the administration of the compounds decreases the plasma level of D-Dimer or Highly Sensitive C Reactive Peptide (hs-CRP), for example, by at least 5%, 10%, 15%, 20%, 25%, 30%, 35%, 40%, 45% 50%, 55%, 60%, 65%, 70%, 75%, 80%, 85%, 90%, 95% or 100% relative to the plasma concentration of D-Dimer or Highly Sensitive C Reactive Peptide (hs-CRP) prior to administration of the compounds.

In certain variations of the above methods, the method may include administering from about 2 mg to about 750 mg of the compound to the subject per day. In other variations, the method may include administering from about 5 mg to about 750 mg of the compound to the subject per day. In other variations, the method may include administering from about 2 mg to about 500 mg of the compound to the subject per day. In other variations, the method may include administering from about 5 mg to about 500 mg of the compound to the subject per day. In certain variations, the method can include administering from about 2 mg to about 250 mg of the compound to the subject per day. In other variations, the method may include administering from about 5 mg to about 250 mg of the compound to the subject per day. In other variations, the method may include administering from about 2 mg to about 100 mg of the compound to the subject per day. In other variations, the method may include administering from about 5 mg to about 100 mg of the compound to the subject per day. In other variations, the method may include administering from about 10 mg to about 75 mg of the compound to the subject per day, for example, administering 10, 25, 50 or 75 mg of the compound to the subject per day.

In certain variations, the compound is administered to the subject for at least 2 weeks, 4 weeks, 6 weeks, 8 weeks, 3 months, 6 months, 1 year, or indefinitely as needed. If the subject is undergoing hemodialysis, the compound may be administered to the subject for a period that includes at least the duration of hemodialysis.

In another variation of the method for treatment of calciphylaxis, in addition to measuring the change/reduction in lesion size following administration of the disclosed compounds, pre and post drug dosing administration, a biopsy may be taken of the relevant lesions using von Kassa Staining to determine tissue levels of PTH and evidence of change in calcium and phosphate deposition in dermal arterioles.

As disclosed herein, the presence of a uremic oxidative blockade is determined by measuring increased plasma lipid peroxidation, e.g., by detection of increased F2 isoprostanes (Morrow et al. (1990) "A series of prostaglandin F2-like compounds are produced in vivo by humans by a non-cyclooxygenase, free radical-catalyzed mechanism," PROC. NATL. ACAD. SCI. USA 87:9383-9387), increased isolevuglandin-plasma protein adducts (Salomon et al. (2000) "Isolevuglandin-protein adducts in humans: Products of free radical induced lipid oxidation through the isoprostane pathway," BIOCHIM BIOPHYS ACTA 1485:225-235), increased breath ethane (Handelman et al. (2000) J AM. SOC. NEPHROL. 11:271A); increased protein and amino acid oxidation, e.g., by detection of tyrosine residue oxidation (Heinecke et al. (1999) "Detecting oxidative modification of biomolecules with isotope dilution mass spectrometry: Sensitive and quantitative assays for oxidized amino acids in proteins and tissues," METHODS ENZYMOL. 300:124-144), cysteine or methionine residue oxidation, lysine oxidation and threonine oxidation, thiol oxidation and carbonyl formation in plasma proteins (Himmelfarb et al. (2000) "Plasma protein thiol oxidation and carbonyl formation in chronic renal failure," KIDNEY INT. 58:2571-2578); reactive aldehyde formation, e.g., by detecting glyoxal, methylglyoxal, acrolein, glycoaldehyde, and parahydroxy phenacetaldehyde (Miyata et al. (1999) "Alterations in non-enzymatic biochemistry in uremia: Origin and significance of 'carbonyl stress' in long-term uremic complications. KIDNEY INT. 55:389-399); increased reactive carbonyl compounds, e.g., by measuring hydrazine formation after reaction with 2,4-dinitrophenylhydrazine; diminished plasma glutathione levels and glutathione peroxidase function (Ceballos-Picot et al. (1996) "Glutathione antioxidant system as a marker of oxidative stress in chronic renal failure," FREE RADIC. BIOL. MED. 21:845-853); and increased ratio of oxidized to reduced thiols (Hultberg et al. (1995) "Reduced, free, and, total fractions of homocysteine and other thiol compounds in plasma from patients with renal failure," NEPHRON 70:62-67; Himmelfarb et al. (2002) "Plasma aminothiol oxidation in chronic renal failure," KIDNEY INT 61:705-716; Ward et al. "Polymorphonuclear leukocyte oxidative burst is enhanced in patients with chronic renal insufficiency," J AM. SOC. NEPHROL. 5:1697-1702).

In another embodiment, there is provided a method of treating, preventing, slowing the progression of, arresting and/or reversing tissue calcification in a pre-diabetic mammal (or subject) with diabetes, chronic kidney disease or a combination thereof, and in need thereof, the method comprising administering to the mammal at least 2 mg of substantially pure compound as disclosed herein per day, to prevent, slow the progression of, and/or arrest tissue calcification, wherein the compound is administered in a pharmaceutical composition. In another aspect of the method, the mammal has diabetes. In yet another aspect, the mammal has type II diabetes; or the mammal has been diagnosed as pre-diabetic. In another aspect, the mammal has chronic kidney disease. In another aspect of the above method, the mammal has stage 4 or 5 chronic kidney disease/end stage renal disease. In yet another aspect, the mammal is undergoing hemodialysis. In another aspect, the mammal is receiving non-warfarin based anti-coagulant therapy. In another aspect, the anti-coagulant therapy is oral anti-coagulation therapy. In another aspect of the method, the anti-coagulation therapy comprises an inhibitor of Factor Xa activity selected from apixaban, rivaroxaban, betrixaban, edoxaban, otamixaban, letaxaban, eribaxaban or fondaparinux; or Factor IIa activity selected from dabigratran or argatroban.

In another embodiment, there is provided a method of treating, preventing, slowing the progression of, arresting, and/or reversing tissue calcification in a mammal undergoing hemodialysis, and in need thereof, the method comprising administering to the mammal at least 2 mg of substantially pure compound as disclosed herein per day, thereby to prevent, slow the progression, arrest, and/or reverse tissue calcification, wherein the disclosed compound is administered in a pharmaceutical composition. In another aspect, the mammal has diabetes.

Vitamin K Metabolism: Development of vascular and soft tissue calcification following the failure to regenerate reduced forms of vitamin K: Vitamin K is an essential enzymatic co-factor that is required for posttranslational modifications of vitamin K dependent (VKD) proteins. While there are numerous VKD proteins many are clinically relevant to ESRD patients. They include central coagulation factors such as factors II VII IX and X as well as intercellular matrix proteins including Matrix GLA-1 and Osteocalcin. Under normal conditions, vitamin K is reduced to vitamin K hydroquinone ($KH_2$) by the enzyme NADPH oxidase. It is only the reduced form of vitamin K that is able to function as a co-factor for gamma glutamate carboxylase (GGCX) which catalyzes the carboxylation of vitamin K dependent proteins. Warfarin blocks the generation of vitamin K hydroquinone by acting as a reductive sink. The enzymatic carboxylation of glutamate residues results in further oxidation of vitamin KH2 to 2-3 epoxide vitamin K (FIG. 2). The final step of the vitamin k cycle requires the enzymatic oxidation of vitamin K 2-3 epoxide back to its native structure. This step is catalyzed by vitamin K oxidative reductase (VKOR) and is a component of the vitamin K cycle that is also blocked by the oxidative effects of Warfarin. The observation that Warfarin blocks both the generation of vitamin K hydroxyquinone (KH2) as well as the regeneration of Vitamin K2 2-3 epoxide helps to explains why the incidence of calciphylaxis and other forms of dystrophic calcification is higher among patients receiving Warfarin therapy.

In one variation, the supplementation of the disclosed compounds and compositions reduces the risk for vascular and soft tissue calcification by increasing the formation of primary calciprotein particles (CPP) composed of Fetuin A and Carboxylated Matrix GLA-1 Proteins. Under normal physiologic conditions plasma calcium and phosphate concentrations are near supersaturation and thus would be expected to precipitate in blood vessels and soft tissue as crystalline hydroxyapatite. The observation that this process does not occur suggests the presence of potent chemical and biologic means for blocking pathologic calcification. Recent studies have shown that circulating calcium phosphate crystals are complexed with two calcification inhibiting proteins to form primary calciprotein particles (CPPs). These protein-mineral complexes are composed of primarily of Fetuin A; a liver derived protein that has been shown to prevent vascular calcification. A second protein in lower quantities is Matrix Gla-1 protein that also functions to prevent pathologic calcification. Matrix Gla-1 is a vitamin K dependent protein and early work by Price et. al and others have shown that formation of the Fetuin-Matrix Gla-1 mineral nanoparticles (primary calciproteins CPP) is dependent upon the gamma carboxylation of Matrix Gla-1. Pre-clinical studies suggest that the calciprotein system functions as an alternative means for preventing pathologic calcification when humoral lines of defense such as pyrophosphate, magnesium and albumin are overwhelmed. The "absorption" of calcium-phosphate crystals by primary CCPs occurs in a coordinated and time-dependent process.

The time to 50% saturation ($T_{50}$) of primary CCPs is an accurate and highly sensitive means for determining the capacity of plasma to "sink" or "absorb" excess calcium phosphate crystals. Patients with a short $T_{50}$ times suggests a reduced capacity to absorb calcium phosphate crystals whereas patients with prolonged $T_{50}$ times are consistent with high capacities. Recent clinical studies have validated the $T_{50}$ test and confirmed that low $T_{50}$ times are associated with increased myocardial infarctions, heart failure and all-cause mortality. Thus, any clinical intervention that can increases the synthesis of circulating primary CCPs will improve the capacity to prevent pathologic calcification. It is noted that because patients with CKD and ESRD exhibits reduced levels of carboxylated Matrix Gla-1 protein and that this process is essential for the formation of primary CPP. Accordingly, supplementation or administration of the disclosed compounds and compositions in CKD or ESRD patients will reduce the risk for pathologic calcification and prevent the development of vascular and soft tissue calcification.

Supplementation or administration of the disclosed compounds or compositions may prevent or slow the development of soft tissue and vascular calcification in dermal tissues by restoring production of Carboxylated Matrix Gla-1 and GAS-6.

The regeneration of Vitamin K involves two key enzymes: vitamin K 2-3 epoxide oxidative reductase (VKOR) and NAD(P)H: quinone oxidoreductase (NQO1). As shown in the figure, VKOR reduces 2-3 Vitamin K epoxide to vitamin K quinone while NADPH reduces Vitamin K quinone to its hydroxyquinone form (KH2). Recent studies have shown that VKOR has two distinct isoforms exist (VKORC-1 and VKORC1-Like-1 [VKORC1-L1]) that differ in both enzymatic properties and tissue distribution. For example, Westhofen et. al has shown that compared to VKORC1, VKOCR-L1 has a 3-fold lower affinity for 2-3 epoxide vitamin K. Subsequent work supported the hypothesis that VKOR-L1 is a specialized isoform that protects against oxidant injury through the regeneration of vitamin K. When cultured HEK 293T cells were incubated with $H_2O_2$, VKOR-L1 expression was increased and evidence of membrane oxidant injury was reduced. The clinical observation that calciphylaxis and vitamin K-dependent vascular calcification are more common in the dermis raises the question of whether there is differential expression of VKOR enzymes in the skin. To address this question, Casper et. al determined mRNA expression of key enzymes involved in regeneration of vitamin K. As shown in FIGS. 3 and 4, skin exhibited the lowest level of VKOR-C1 than any other tissue. Moreover, expression of NADPH in the dermis was below the level of detection. These observations suggest that any condition or procedure (i.e. hemodialysis) that blocks re-constitution of vitamin K predisposes that tissue to pathologic calcification.

We note that the oxidative properties of uremic plasma as well as the oxidative effects of dialysis itself results in a "metabolic block" and an accumulation of 2-3 epoxide vitamin K and a reduction in the intracellular levels of vitamin K2. The "down-stream" effects of this blockade includes the inability to gamma carboxylate key proteins involved in preventing soft tissue and vascular calcification. We further note that the oxidative effects of hemodialysis exacerbates this effect which may explain in part the predilection of ESRD patients to develop calciphylaxis and vascular calcification.

The relationship between vitamin K and circulating vitamin K dependent proteins in CKD-ESRD Patients: It is widely recognized that despite dietary deficiencies, vitamin K levels among ESRD patients may not be reduced. For example, Holder et. al studied 172 stable dialysis patients and found that only 6% of patients exhibited a clinically significant deficiency in vitamin K. However, when patients were examined for the level of carboxylated osteocalcin, a full 60% of patients has reduced levels. To confirm that was a general effect of reduced vitamin K activity, the authors also measured PIVKA-II; another vitamin K dependent protein. Indeed, a full 90% of both CKD and ESRD patients were found to have reduced levels of carboxylated pro-thrombin. In a similar study, Pilkey et. al measured the vitamin K1 levels in 142 ESRD patients and found that the majority of patients had adequate vitamin K stores but 93% of patients had uncarboxylated osteocalcin levels that were greater than 20% of total levels. It is noted that there was no correlation between total vitamin K1 and the levels of circulating of uncarboxylated osteocalcin. This unexpected finding is consistent with the hypothesis that in uremic patients, total vitamin K levels can be normal while generation of reduced forms are blocked by the oxidative properties of uremia.

In one variation, the supplementation or administration of the disclosed compounds and compositions will reverse hemodialysis induced inhibition of vitamin K dependent proteins through normalization of functional reduced forms of vitamin K. The observation that oxidant conditions can disrupt the vitamin K cycle suggests that the oxidant load generated during hemodialysis could contribute to the high rates of vascular and soft tissue calcification observed within the ESRD population. Work by Himmelfarb et. al and others have confirmed that the simply delivery of hemodialysis can lead to the oxidation of numerous tissue proteins. For example, hydroxyl amino acid side chains be oxidized to oxidized to carbonyl groups. In a study of CKD and ESRD patients, Himmelfarb et. al demonstrated using carbonyl side chain oxidation as a measure of global oxidant burden, Himmelfarb et. al demonstrated that both CKD and ESRD patients exhibit a higher percentage (15-fold) (See FIG. 5) of carbonyl proteins compared to normal controls. The percentage of carbonyl proteins was even higher among patients receiving dialysis demonstrating that not only does dialysis reduce oxidant burden, it appears to contribute to it. As shown in FIG. 5, patients with uremia were found to have up to 15-fold higher levels of carbonylated proteins. Accordingly, the oxidative load generated by the delivery of hemodialysis leads to oxidation of the function vitamin K hydroquinone (KH2) to the non-functional native vitamin. The oxidation of KH2 by hemodialysis block its ability to function as a co-factor for GGCX which down-stream leads to reduced gamma carboxylation of vitamin K dependent proteins.

To confirm that uremia and hemodialysis disrupts the vitamin K cycle, the ratio of vitamin K quinone to 2-3 epoxide vitamin K and vitamin K hydroxyquinone (KH2) may be determined in patients with normal renal function, CKD (Stage IV & V) and ESRD patients. To determine whether the very process of hemodialysis further disrupts the vitamin K cycle, we can measure the levels of oxidized vitamin K in immediately prior to hemodialysis, then at mid-dialysis (2 hrs) and 30 minutes post dialysis. Previous studies examining the interactions between Warfarin and vitamin K metabolism have shown that 2-3 Epoxide Vitamin K are readily measured. Compared to controls, patients with CKD and ESRD will have higher levels of 2-3 epoxide vitamin K and lower levels of vitamin hydroquinone (KH2). To determine whether a loss of reduced forms of Vitamin K (KH2) leads to a reduction in the carboxylation of vitamin K dependent proteins, we can measure the levels of the following biomarkers in control, CKD (Stage IV and V) and ESRD (Pre-Post hemodialysis). Matrix GLA-1 protein; Growth Arrest Specific Gene 6 (Gas-6) proteins; PIVAK-II protein; Osteocalcin; Protein C; Protein S; Fetuin A; and Osteoprotegerin (Dialysis Plasma Levels: 6.7±2.2 pmole/L. We extend these studies by including patients receiving stable 3x/week hemodialysis. The levels of carboxylated and uncarboxylated vitamin K dependent proteins in pre-dialysis serum ma be compared levels obtained at hour 2 and the end of a dialysis session. The oxidative effects of dialysis itself will lead to a reduction in the level of carboxylated Vitamin K dependent proteins.

In one variation, the supplementation with the disclosed compounds and compositions in ESRD patients with Calcific Uremic Arteriolopathy (Calciphylaxis) will reduce the time of wound healing by preventing calcification of new blood vessels and restoring blood flow: Skin Biopsies: To confirm that supplementation of the disclosed compounds and compositions prevents the development of small vessel calcification and dermal ischemia, we may identify patients with calciphylaxis confirmed by dermal skin biopsy and randomize patients to treatment with menaquinone-7 or placebo. Clinical Endpoints may include the following: 1) Time to Wound Vacuum therapy withdrawal and 2) time for wound healing defined as the time needed for a 50% reduction in collective the surface area of all calciphylaxis wounds.

Histopathologic Endpoints: Comparison of Diagnostic dermal biopsy with Protocol repeat dermal biopsy after 12 weeks of Menaquinone-7 therapy. Change in the level of interstitial calcium deposition defined as the change in Von Kossa staining, which may be be quantified by digital image color analysis. We may use dermal biopsies to validate the biomarkers at the tissue level. This enable the confirmation of the preventive properties of EPN-701 on early vascular calcification. The validation of these biomarkers at the tissue will also enable clinicians to utilize the biomarkers as means to track clinical responsiveness. Calcification of microvasculature precedes development of CUA lesions. The level of calcification will be quantified by Von Kossa calcium staining in the peripheral tissue and normalized as calcium content per unit area. We may use the Von Kossa as a means of confirming the preventive properties of EPN-701 on the development of vascular calcification.

In one variation, the supplementation of the disclosed compounds and compositions in ESRD patients with Calcific Uremic Arteriolopathy (Calciphylaxis) will reduce the time of wound healing by normalizing carboxy Protein C levels in the dermis and preventing primary thrombosis of dermal blood vessels. Accordingly, in one variation, the supplementation or administration of the disclosed compounds or compositions in diabetic patients will prevent the development of vascular dementia by preventing calcification and development of small vessel vasculopathy.

In yet another embodiment, there is provided a fortified food or drink formulation comprising adding to the food or drink a composition comprising a compound of any one of the above compounds, or a mixture thereof.

Also included in the above embodiments, aspects and variations are salts of amino acids such as arginate and the like, gluconate, and galacturonate. Some of the compounds of the invention may form inner salts or zwitterions. Certain of the compounds of the present invention can exist in unsolvated forms as well as solvated forms, including hydrated forms, and are intended to be within the scope of the present invention. Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols, or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

As disclosed herein, the disclosed compounds and compositions may include a solubility enhancer or solubilizer selected from oleic acid, Kolliphor® EL (polyoxyl castor oil or Cremophor EL), Vitamin E TPGS (D-α-tocopherol polyethylene glycol-1000 succinate), Maisine® CC (glyceryl monolinoleate), Gelucire® 44/14 (lauroyl polyoxyl-32 glycerides), Miglyol® 812N (esters of saturated coconut and palm kernel oil-derived caprylic fatty acids and glycerin), Plurol® Oleique (Polyglyceryl-6 Dioleate), Lauroglycol™ 90 (propylene glycol monolaurate (type II), Labrasol® (Caprylocaproyl polyoxyl-8 glycerides), Kolliphor® EL (polyoxyl castor oil), Captisol® (SBE-beta-cyclodextrin), Encapsin™ HPB (hydroxypropylbeta-cyclodextrin), Peceol™ (glycerol/glyceryl monooleate (type 40)), sodium deoxycholate, deoxycholic acid, Labrafil® M2125CS (linoleoyl Polyoxyl-6 glycerides) and medium-chain mono- and diglycerides.

In one variation, there is provided the compounds disclosed herein, or a pharmaceutically acceptable salt thereof, optionally in the form of a single stereoisomer or mixture of stereoisomers thereof; and compositions comprising the compounds.

In addition to the exemplary embodiments, aspects and variations described above, further embodiments, aspects and variations will become apparent by reference to the drawings and figures and by examination of the following descriptions.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustrative in the figures and drawings, and it is intended that the embodiments, aspects and variations, and the figures and drawings disclosed herein are to be considered illustrative and not limiting.

As used herein, a "PEG" group is a polyethylene glycol compound known and commercially available in the art. PEG is usually a mixture of oligomers characterized by an average molecular weight. In one example, the PEG has an average molecular weight from about 200 to about 5000. In another aspect, PEG has an average molecular weight from about 500 to about 1500. In another aspect, PEG has an average molecular weight from about 500 to about 800 or about 900 to about 1200. In one example, the PEG is PEG-600 or is PEG-750. Both linear and branched PEG moieties can be used in the present application. In one aspect, PEG has between 1000 and 5000 subunits. In one aspect, the PEG is PEG 1000. In another aspect, PEG has between 100 and 500 subunits. In yet another aspect, PEG has between 10 and 50 subunits. In one aspect, PEG has between 1 and 25 subunits. In another aspect, PEG has between 15 and 25 subunits. PEG has between 5 and 100 subunits. In another aspect, PEG has between 1 and 500 subunits.

Similarly, an "MPEG", "M-PEG" or "m-PEG" group is a polyoxyethanyl moiety (PEG) capped with a methyl group (methoxypolyoxyethanyl or mPEG). Accordingly, a number followed by the abbreviation "Me" (e.g., -1000 Me) indicates that the PEG is capped with a methyl group, rather than a hydroxyl group, —OH.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

"Therapeutically effective amount" means an amount of a compound or drug that elicits any of the biological effects listed in the specification.

EXPERIMENTAL

Figure 1:
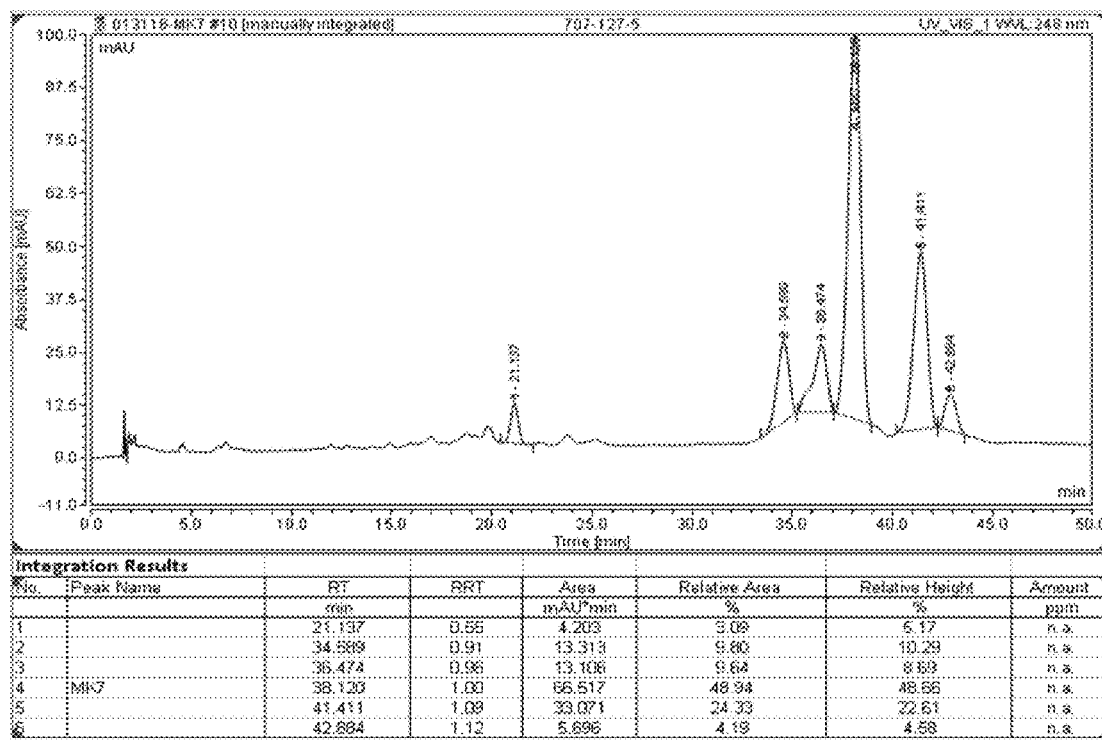
FIG. 1 is a representation of a chromatogram of menaquinone-7 and its regioisomer shown with a ratio of 3:1, as determined by $^1$H NMR.
Figure 2:
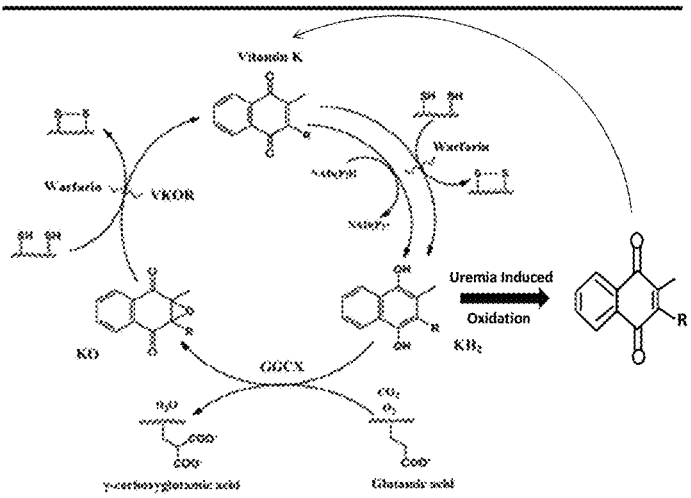
FIG. 2 is a scheme showing the uremia and dialysis induced oxidation of KH2 functional carboxylation of vitamin K dependent proteins.
Figure 2:
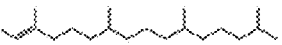
Figure 3:
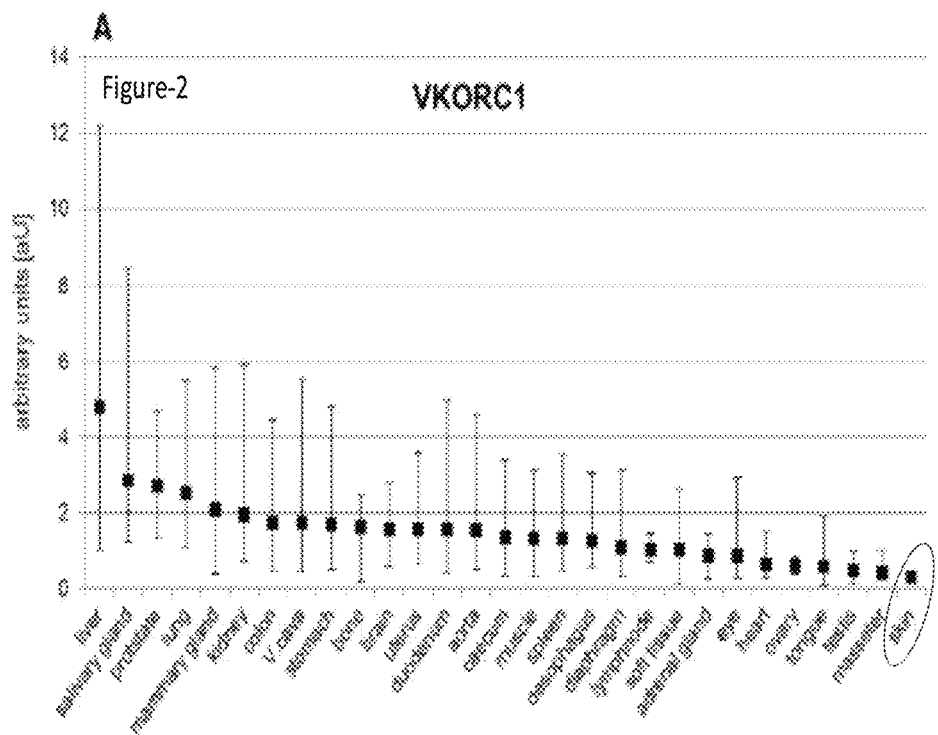
FIG. 3 is graph showing the VKORC1 in arbitrary units and specific tissues.
Figure 4:
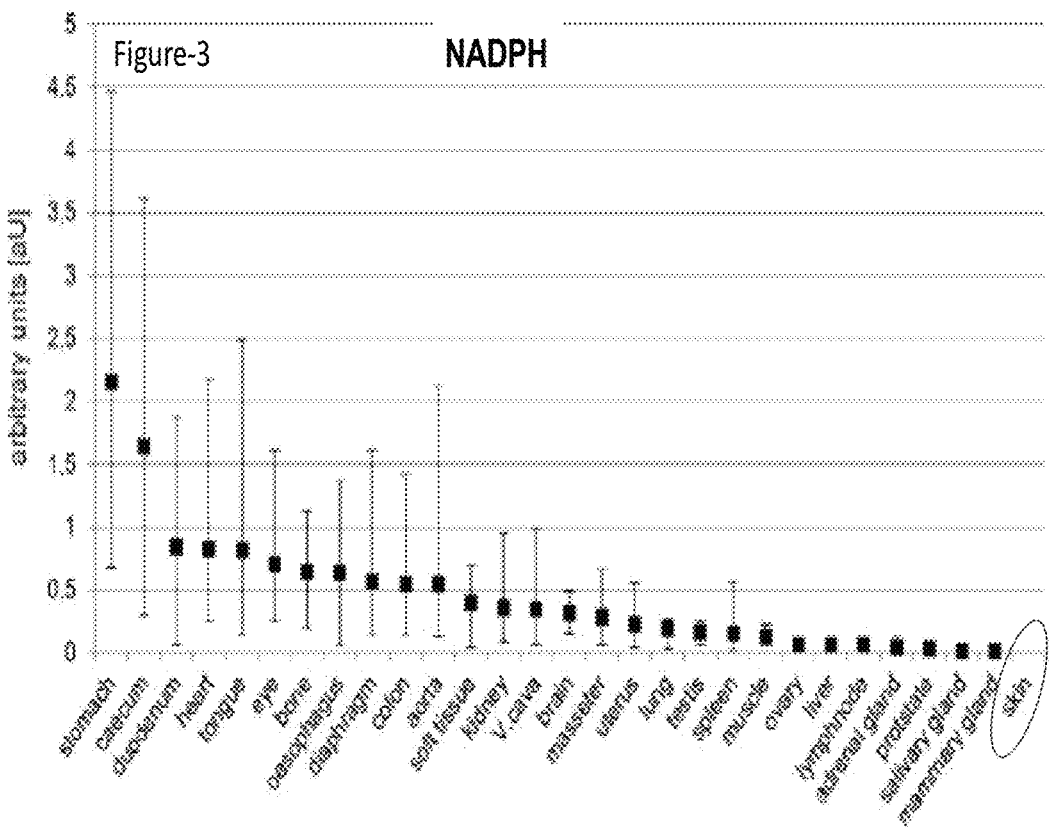
FIG. 4 is a graph showing the NADPH in arbitrary units and specific tissues.
Figure 5:
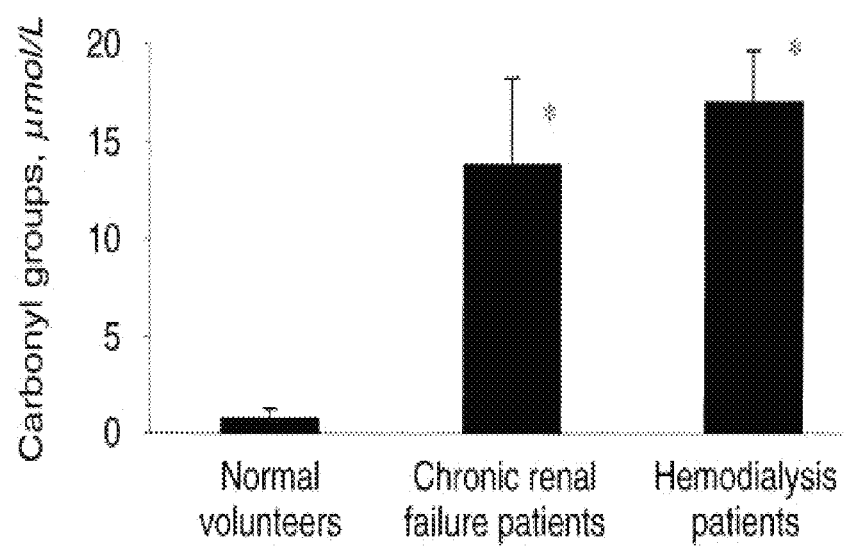
FIG. 5 is a graph showing CKD and ESRD patients exhibit a higher percentage of carbonyl proteins compared to normal controls.

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Preparation of Menaquinol-7:

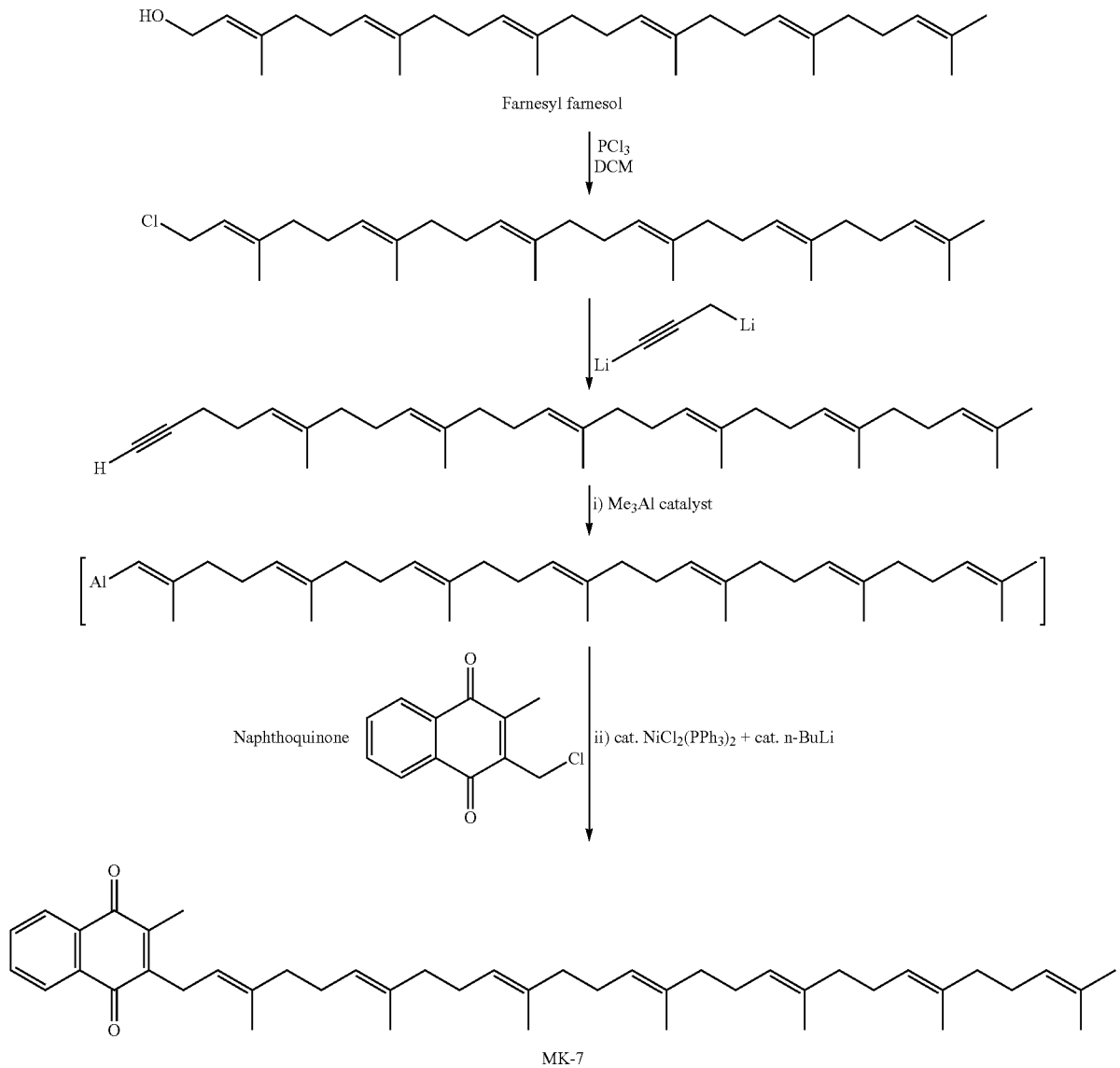

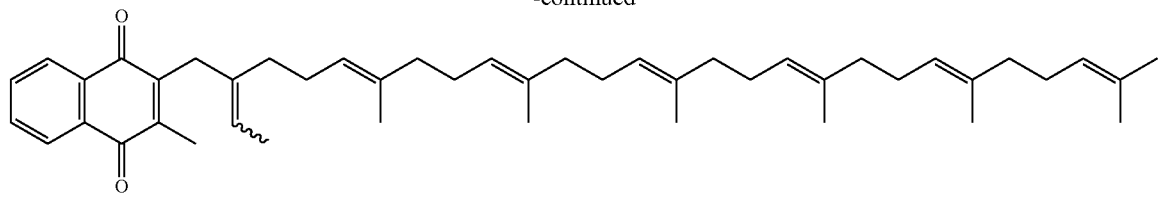

Regiosiomer(s) of MK-7

Preparation of Menaquinol-7: Use of a Farnesylfarnesol-Derived Alkyne and its Subsequent Ni-Catalyzed Coupling/Reduction Reaction:

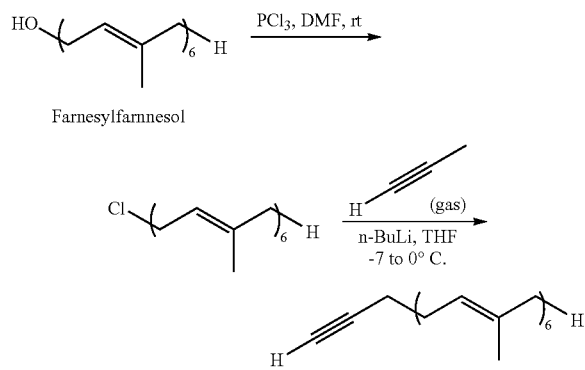

Preparation of farnesylfarnesol-derived alkyne: As described for the farnesol-derived alkyne synthesis, farnesylfarnesol (10 g,) was converted to the corresponding chloride using PCl$_3$/DMF conditions. Crude chloride (10.4 g made) was obtained in 100% yield and it was sufficiently pure by $^1$H NMR. The crude chloride (8.9 g) was treated with dilithiopropyne and the resulting crude alkyne was purified on a Biotage chromatography instrument. The alkyne was obtained as a colorless oil, 6.2 g in 69% isolated yield. Q-NMR analysis indicated that the purity of the alkyne as 94.0 wt %. This product was used as it is for the next step without further purifications (no plug filtration nor distillation). Some residual alkyne was retained in the column and was flashed out with a stronger solvent (10% EtOAc/hexane) to afford 1.6 g (18%) of additional alkyne product as a yellow oil.

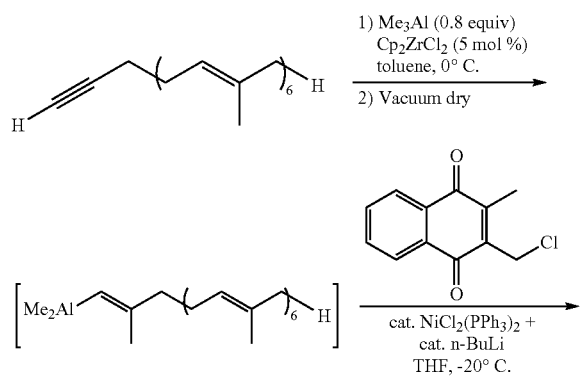

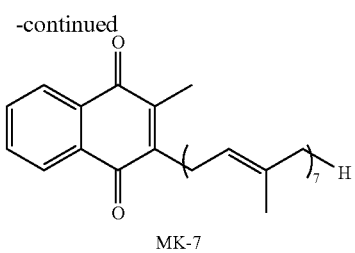

MK-7

Ni-catalyzed coupling: Me$_3$Al (2 M in toluene, 1.5 mL, 3.0 mmol, 1.5 equiv) was added to Cp$_2$ZrCl$_2$ (29 mg, 0.10 mmol, 5 mol %) at 0° C. To this solution was added alkyne (898 mg, 2 mmol, 1 equiv) at 0° C. After stirring at 0° C. for 1 h, TLC indicated most of the alkyne was consumed. GC/MS assay was also used to monitor this conversion process. The mixture was gently vacuumed using high vacuum pump at ambient temperature to remove excess Me$_3$Al and some toluene. When the mixture became viscous, vacuum was stopped, leaving some residual toluene. If all of the toluene was removed by vacuum, an exothermic reaction to about 35° C. was observed. The residue was cooled to −20° C. and THF (2 mL) was added to the mixture. To this solution was added a THF (2 mL) solution of naphthoquinone (440 mg, 2.00 mmol, 1 equiv, lot # AP56079013-006-01). The syringe was rinsed with additional THF (1 mL) and it was added to the mixture. In a separate flask, NiCl$_2$(PPh$_3$)$_2$ (39 mg, 0.06 mmol, 3 mol %) was suspended in THF (1 mL). To this was added n-BuLi (2.1 M in hexane, 57 μL, 0.12 mmol, 6 mol %) and the resulting light yellow solution was stirred for 1 min before it was transferred to the above vinylalane and naphthoquinone mixture at −20° C. The resulting dark mixture was stirred at −20° C. for 3 h. The reaction was monitored by TLC where no change was observed after being stirred for 1 h at −20° C. The mixture was carefully quenched by the addition of cold water and 0.2 N HCl solution and then extracted with MTBE. The crude oil (1.1 g) was monitored by $^1$H NMR and it indicated that the ratio of desired isomer and the regioisomer was 96:4. Crude material was purified via Biotage chromatography to give 840 mg of menaquinone-7 in 65% isolated yield along with recovered naphthoquinone (150 mg, 34%). The product was isolated by chromatography and the ratio of the isomers was 96:4 by $^1$H NMR.

Synthesis of MK-7 using reduced amounts of Me$_3$Al:

Me$_3$Al (2 M in toluene, 1.2 mL, 2.4 mmol, 1.2 equiv) was added to Cp$_2$ZiCl$_2$ (29 mg, 0.10 mmol, 5 mol %) at 0° C. To this solution was added the alkyne (898 mg, 2 mmol, 1 equiv) at 0° C. After stirring at 0° C. for 1 h, TLC indicated most of the alkyne was consumed. GC/MS assay was used to monitor the reaction progress. The mixture was gently placed under vacuum using high vacuum pump at ambient temperature in order to remove excess Me$_3$Al and some toluene. When the mixture became viscous, vacuum was stopped, leaving some residual toluene. (It was noted that if substantially all of the toluene was removed by vacuum, an exothermic reaction to about 35° C. was observed). The residue was cooled to −20° C. and THF (2 mL) was added to the mixture. To this solution was added a THF (2 mL) solution of naphthoquinone (440 mg, 2.0 mmol, 1 equiv, lot # AP56079013-006-01). The syringe was rinsed with additional THF (1 mL) and it was added to the mixture. In a separate flask, $NiCl_2(PPh_3)_2$ (39 mg, 0.06 mmol, 3 mol %) was suspended in THF (1 mL). To this was added n-BuLi (2.1 M in hexane, 57 µL, 0.12 mmol, 6 mol %) and the resulting light yellow solution was stirred for 1 min before it was transferred to the above vinylalane and naphthoquinone mixture at −20° C. The resulting dark mixture was stirred at −20° C. for 1 h. $^1H$ NMR of the crude mixture indicates that the ratio of MK-7 and the regioisomer was 93:7. $^1H$ NMR also indicated that the formation of terminal olefin was less compared to the crude mixture that used 1.5 equiv of $Me_3Al$. It was purified by Biotage chromatography to give 0.97 g of pure MK-7 in 75% isolated yield. 52 mg of unreacted naphthoquinone (12% yield) was recovered. $^1H$ NMR indicated that the ratio of MK-7 and regioisomer was unchanged.

Synthesis of MK-7 with Reduced $Me_3Al$:

$Me_3Al$ (2 M in toluene, 1.2 mL, 2.4 mmol, 1.2 equiv) was added to $Cp_2ZiCl_2$ (29 mg, 0.10 mmol, 5 mol %) at 0° C. To this solution was added alkyne (900 mg, 2 mmol, 1 equiv) at 0° C. After stirring at 0° C. for 1 h, TLC indicated most of the alkyne was consumed. GC/MS assay was also used to monitor the reaction progress.

The mixture was cooled to −20° C. To this was added THF (2 mL) and a THF (2 mL) solution of naphthoquinone (440 mg, 2.00 mmol, 1 equiv, lot # AP56079013-006-01). The syringe was rinsed with additional THF (1 mL) and it was added to the mixture. In a separate flask, Ni(0) catalyst was prepared as above, and it was transferred to above vinylalane and naphthoquinone mixture at −20° C. The resulting dark mixture was stirred at −20° C. for 1 h. $^1H$ NMR analysis of the crude mixture indicated that the coupling reaction was nearly completed and the ratio of MK-7 and the regioisomer was 93:7. Comparing all the crude $^1H$ NMR overlaid spectra in the above descriptions, this reaction provided the cleanest conversion. The mixture was purified on Biotage chromatography to give 1.02 g of pure MK-7 in 78% isolated yield, with a recovery of 64 mg (15%) of unreacted naphthoquinone. This process demonstrated that the removal of $Me_3Al$ and toluene from the carboalumination mixture prior to the subsequent Negishi coupling reaction is not necessary.

Recrystallization of Menaquinone-7:

Chromatographed material (0.98 g, ratio of menaquinone-7 and the regioisomer was 93:7) was recrystallized using various solvents (toluene, dichloromethane, hexanes, heptanes, THF, methanol, ethanol, propanol, iso-propanol, MTBE, MEK, DMF and their various mixtures of binary and ternary solvent mixtures) in different ratios did not provide a significant improvement of the regioisomeric ratio. However, the chromatographed menaquinone-7 was recrystallized from EtOAc/EtOH (1:5) provided 0.66 g (67%) of clean menaquinone-7. HPLC indicates that the ratio of MK-7 and regioisomer was 99.8:0.2. Mother liquor was concentrated to give 0.26 g (26%) of oil and regioisomer was enriched, showing the effectiveness of the crystallization solvent mixture to optimize the isolation of the desired isomer.

Large Scale Reactions:

The present reaction was performed using 1.2 equiv of $Me_3Al$ with no vacuuming before the coupling reaction. Farnesylfarnesol (50 g) was chlorinated using the standard method noted above, and a modified workup procedure was used. $PCl_3$ (7.2 mL, 82 mmol, 0.7 equiv) was carefully added to DMF (240 mL) at 10° C. and vigorously stirred for 30 min. To this was added a DMF (30 mL) solution of farnesylfarnesol (50 g, 117 mmol) using an addition funnel. The addition funnel was rinsed with additional DMF (30 mL) and the DMF rinse was added to the mixture. The resulting orange suspension was stirred for 1 h at 10° C. and stirred for 1 h at ambient temperature. Because the DMF solution of farnesylfarnesol was a very thick and viscous solution, the preparation of the farnesylfarnesol solution may also be prepared in n-heptane to provide a less viscous solution for processing and transfer at a large scale.

The reaction was monitored by LCMS until the farnesylfarnesol was consumed. The product was extracted with n-heptane, dried over $MgSO_4$ and concentrated under reduced pressure (20 mm Hg, bath temp 38° C.). Some residual n-heptane was allowed to remain in the chloride mixture to reduce the evaporation and loss of the chloride. The mixture was obtained in 62.5 g of clear oil. $^1H$ NMR indicated 49.6 g (95%) of desired chloride and 12.9 g of n-heptane. This mixture was used as it was for the next reaction without further purifications.

Preparation of the Alkyne:

Dilithiopropyne was prepared in the same manner as described above. Accordingly, instead of charging all the n-BuLi solution before propyne gas was introduced, half of n-BuLi was added. After excess propyne gas was introduced, the mixture was stirred at ambient temperature to allow the excess propyne gas to evaporate. To the resulting propyne acetylide was added another one equivalent of n-BuLi to form dilithiopropyne. After addition of the above crude chloride (49.6 g) and the reaction was quenched, a 1:1 mixture of desired alkyne and unreacted chloride was obtained. It is noted that excess propyne gas remained in the THF solution so that the preparation of dilithiopropyne was incomplete. The chloride decomposes in GCMS and gave multiple peaks. The chloride and the alkyne appeared at the same retention time. The material was re-subjected to the dilithio-alkyne displacement.

Accordingly, the dilithiopropyne was prepared again, but a scale was placed in the hood to weigh and monitor the weight of gaseous propyne when it was introduced to the n-BuLi solution. To the resulting dilithiopropyne was added the above mixture of alkyne and chloride in several portions while monitoring the reaction aliquot by $^1H$ NMR, until all chloride converted to the alkyne. The resulting crude yellow oil (60 g) was monitored by $^1H$ NMR and shown to provide an essentially pure desired alkyne and n-heptane. GCMS data indicated that, in addition to the alkyne, the n-butyl adduct (m/z 466.84), which was derived from the excess n-BuLi displacement of the chloride. The crude alkyne was passed through a gravity grade silica-gel plug and the filter cake was rinsed with 5% MTBE/n-heptane. After evaporation of the filtrate, 56.4 g of clear oil (theoretical yield: 49.8 g) was obtained. $^1H$ NMR indicated it was a mixture of desired alkyne and n-heptane and the purity was 76 wt %. This material was used as is for the carboalumination without further purification.

The reaction using the above impure alkyne was slower compared to the previously made, purer alkyne. This batch of alkyne required 3 to 4 hours to complete compared to within 1 h with more thoroughly chromatographed and pure alkyne. Reaction using distilled and pure farnesylfarnesol:

100 mg of the above distilled residue of farnesylfarnesol was used for the coupling reaction using the above cited standard procedure. The reaction was completed within 15 min. It was noted that the reason for the slower conversion observed above was the presence of the volatiles (likely n-heptane) that were removed to provide pure farnesulfarnesol by applying vacuum and heat, as noted above. The n-Butyl adduct did not interfere and the presence of n-Bu adduct was not the cause of slower conversion. Fractions were monitored by GCMS and the fractions that contained pure alkyne peak were collected. 6 g of n-butyl adduct and 29 g of alkyne was obtained. Since the alkyne is not volatile, it was vacuum dried at 50° C. by rotary evaporator (10-12 mmHg) for 30 min. This material was pure by GCMS, and $^1$H NMR indicated a small impurity that may be a dimer of the chloride resulting from an attachment of a carbon-carbon bond. The Q-NMR suggested that the alkyne was 68 wt % pure.

Preparation of Menaquinone-7 Using Pure Alkyne:

A 10 g reaction scale was performed using the starting alkyne containing some unknown impurities. Accordingly, 10 g of alkyne (14.7 g of impure alkyne as is, 61 wt %, 20.0 mmol) was treated with 1.2 equiv of Me$_3$Al in toluene in the presence of Cp$_2$ZiCl$_2$ (5 mol %) at 0° C. GCMS indicated that the reaction was completed within 1 h. The subsequent coupling reaction was carried out using 1 equiv of naphthoquinone (4.4 g, 20 mmol) at −20° C. for 1 h. A reaction aliquot was monitored by $^1$H NMR and indicated naphthoquinone was nearly consumed. $^1$H NMR and HPLC both indicated that the ratio of menaquinone and its regioisomer was 94:6. The reaction mixture was quenched and extracted with n-heptane. The organic layer was passed through a silica-gel plug and the plug was rinsed with 5% EtOAc/n-heptane. Filtrates were concentrated to give crude oil (21.3 g) which was recrystallized from EtOAc (20 mL) and EtOH (100 mL) to provide 15.7 g of solid (theoretical yield: 14.5 g). HPLC indicated that the ratio of desired product to the regioisomer was 97:3. Q-NMR showed a purity of 72 wt %. This product contains 11.3 g (78%) of menaquinone-7. The solid was stirred in n-BuOH (25 mL) at 0° C. and it was filtered. Filter cake was rinsed with cold n-BuOH and the filter cake was dried in vacuo to afforded 9 g of pure material in 62% overall isolated yield. HPLC indicated that the ratio of menaquinone and regioisomer was 99.8:0.2, with a purity of >99.6% by HPLC using an external standard. HPLC Conditions: Column: Thermo Acclaim C30, 250×2.1 mm, 3 μm (Part #078664); Column temperature: 15° C.; Mobile phase: 2% water in methanol; Diluent: 90% IPA in THF; Detector: UV 248 nm, 234 nm; Flow rate: 0.4 mL/min; Injection volume: 4 μL Running time: 50 min.

Reduction of MK-7 Followed by Esterification of Menaquinol-7:

The menaquinol compounds and derivatives, such as menaquinol-7 compounds and derivatives, may be prepared according to the general scheme as described below. Such acylated compounds may be symmetrical, wherein both hydroxyl groups of the menaquinol are acylated, or only one of the two hydroxyl groups, either the 5-position or the 8-position, are acylated, and the other remaining as the hydroxyl group of the menaquinol.

Accordingly, the menaquinone, such as MK-7, may be contacted with a metal, such as zinc, and an acid, such as acetic acid or dilute HCl, in a protic solvent, such as methanol or ethanol, for a sufficient time under condition to form the corresponding menaquinol intermediate. The menaquinol may be isolated before taking the acylation reaction, or the menaquinol may be acylated in situ with an acid halide (X=Cl, Br, I) or an acylating agent such as an acid anhydride in a solvent, to form the corresponding mono- or di-acylated menaquinol derivative. In one variation of the method, the acid anhydride may be a symmetrical or an unsymmetrical or mixed acid anhydride, to form the corresponding mono- or diacylated menaquinol.

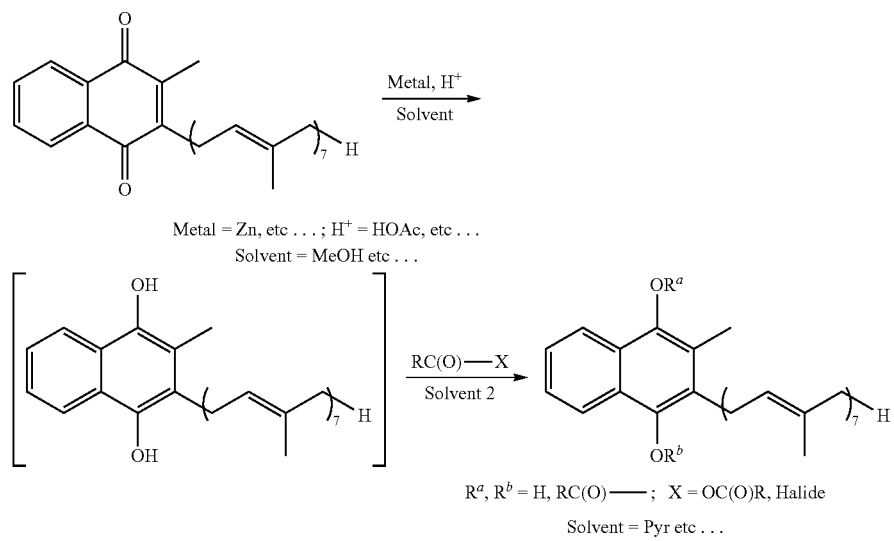

To a round-bottom flask is added MK-7 (0.15 g, 0.23 mmol, 1 equiv), zinc powder (0.1 g, 1.5 mmol, 6.5 equiv), and acetic acid (0.2 mL) in methanol (1 mL). The reaction is stirred at room temperature. After the reaction is complete, the reaction is concentrated by exposure to high vacuum to remove all volatiles, and then diluted with pyridine (1 mL). To this mixture is then added the acylating agent (2.2 equiv) and the mixture is allowed to stir at rt until the hydroquinone is consumed. The reaction mixture is then diluted with hexanes and filtrated through Celite. The solution is then washed with a 1M HCl aqueous solution (2×20 mL) and then saturated aqueous Na$_2$CO$_3$ solution. The organic layer is dried over anhydrous MgSO$_4$, filtered and concentrated in vacuo to yield the diacylated product. Further purification could be accomplished via recrystallization or column chromatography.

To a round-bottom flask was added MK-7 (0.15 g, 0.23 mmol, 1 equiv), zinc powder (0.1 g, 1.5 mmol, 6.5 equiv) and pyridine (0.8 mL, 9.9 mmol, 43 equiv) in acetic anhydride (3 mL, 138 equiv). The reaction was stirred for 0.5 h at room temperature (at t=0 h, MK-7 is poorly soluble and the mixture is yellow; after completion, the product is well dispersed and the solution is brown). The reaction was diluted with hexanes (40 mL) and filtrated through Celite. The organic layer was washed in succession with a 1M HCl aqueous solution (2×20 mL) and saturated $Na_2CO_3$ aqueous solution. The organic layer was dried over anhydrous $MgSO_4$, filtered and concentrated in vacuo to yield a pale yellow oil (915 mg, 91%). $R_f$=0.46 (9:1 hexanes/$Et_2O$). $^1$H NMR (500 MHz, $CDCl_3$) δ 7.74-7.63 (m, 2H), 7.50-7.43 (m, 2H), 5.19-5.01 (m, 7H), 3.42 (s, 2H), 2.49 (s, 3H), 2.47 (s, 3H), 2.25 (s, 3H), 2.16-1.89 (m, 23H), 1.79 (s, 3H), 1.69 (s, 3H), 1.61 (s, 17H), 1.59 (s, 17H), 1.55 (s, 5H). $^{13}$C NMR (126 MHz, $CDCl_3$) δ 169.5, 169.1, 142.7, 142.4, 136.4, 135.3, 135.0, 135.0, 135.0, 135.0, 131.3, 130.4, 127.1, 126.4, 126.4, 126.3, 126.3, 124.5, 124.4, 124.4, 124.3, 124.0, 121.5, 121.3, 121.2, 39.9, 39.9, 39.8, 39.7, 29.8, 27.2, 26.9, 26.8, 26.8, 26.8, 26.7, 25.8, 20.8, 20.7, 17.8, 16.5, 16.2, 16.1, 16.1, 13.2.

Reduction of menaquinone: In a two neck round bottom flask fitted with a condenser, a nitrogen purge tube and a magnetic bar is added 10 mL of methanol and toluene mixture (70:30) and 0.93 g ammonium formate dissolved in 1 mL water. Pd-carbon (10%) 100 mg was added after stirring for 15 min under nitrogen followed by the menaquinone (10 mmol) after about 30 seconds. The mixture is stirred for 4 h at room temperature. The catalyst is removed by filtration through a sintered disk under suction and the filtrate evaporated under reduced pressure to give about 2 g of crude solid product. The residue is extracted with dichloromethane and the extract may be used in the acylation step without further purification or isolation.

Depending on the reaction conditions and stoichiometry of the acylating reagent relative to the menaquinol, the formation of the mono acylated product, such as 30 and 3, or the diacylated product 32, may be prepared selectively. Accordingly, an excess of the acylation reagent will drive the reaction toward the formation of the diacylated product 32; whereas the use of less than one equivalent of the acylation reagent under the appropriate conditions will provide the mono-acylated product.

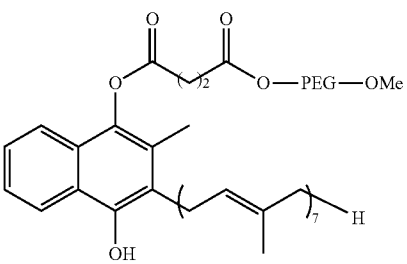

30

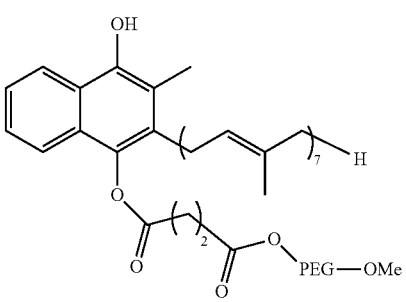

31

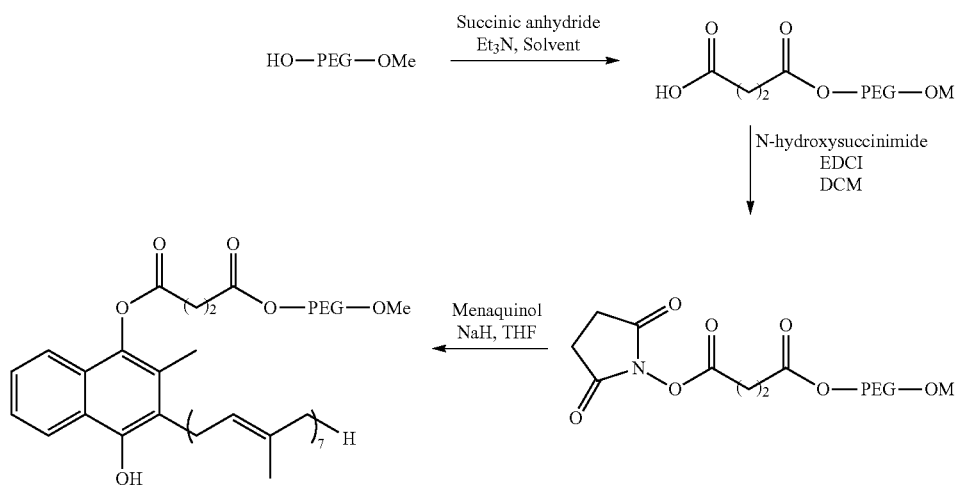

-continued

32

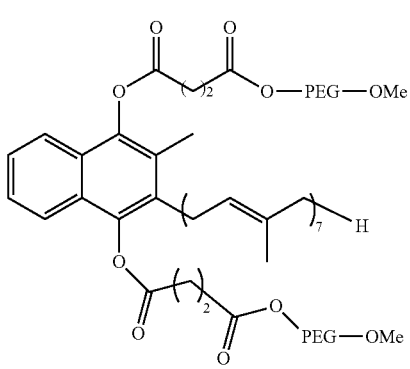

The preparation or coupling reaction with water soluble PEG groups:

The formation of MPEG derivatives of menaquinol leads to water solubilization of the menaquinol compounds. In one variation, the MPEG derivatives may be prepared with an initial treatment with an anhydride, such as succinic anhydride, to form the ester acid derivative. The ester acid derivative may be isolated, and then treated with an MPEG compound to form the diesters.

To a solution of poly(ethylene glycol) monomethylether-2000 (15 g, 7.5 mmol) and succinic anhydride (1.5 g, 15 mmol) in tolune (7.5 mL) and Et$_3$N (0.53 mL, 3.75 mmol) is added at RT, and the reaction mixture is stirred at about 60° C. for abut 8 hours until the reaction was complete. Water (15 mL) is added to the reaction mixture and the mixture is extracted with DCM (3×25 mL). The combined organic layers were washed with 1 N HCl (3×50 mL) and then with brine (2×30 mL) and then dried over anhydrous Na$_2$SO$_4$. The solution is concentrated under rotoevaporation to afford the poly(ethylene glycol) monomethyl ether-2000 succinate in about 99% yield (15.6 g) as a solid.

Preparation of activated PEGylated Succinic Acid: Poly (ethylene glycol) monoethyl ether-2000 succinate (2.1 g, 1 mmol) is dissolved in DCM (10 mL) and cooled to 0° C. N-Hydroxysuccinimide (0.14 g, 1.2 mmol) and 1-(3-dimethylaminopropyl)-3-ethyl carbodiimide (EDCI, 0.25 g, 1.3 mmol) is directly added in succession to the reaction mixture as solids. The resulting solution is stirred at RT for about 12 hours. Water (15 mL) is added to the reaction mixture and the product is extracted with DCM (3×20 mL). The combined organic layers are washed with water (3×20 mL), brine (2×20 mL), dried over anhydrous Na$_2$SO$_4$ and concentrated via rotoevaporation to provide the product (2.17 g, 99%) as an off white, waxy solid.

NaH (0.026 g, 0.65 mmol, 60% suspension in mineral oil) is added to a stirred solution of menaquinol (0.6 mmol) in THF (5 mL) at 0° C. After the addition, the reaciton mixture is stirred at 20° C. for about 1 hour. A solution of the poly(ethylene glycol) monomethyl ether-2000 succinate (0.50 mmol) in THF (50 mL) is added to the mixture at 0° C., and the reaction is stirred for 30 minutes. The mixture is stirred for another 8 hours at RT. The reaction is cooled to 0° C. and saturated aqueous NH$_4$Cl (15 mL) is added and then extracted with DCM (3×20 mL). The combined organic layers are washed with water (2×20 mL) and brine (2×15 mL), and the organics are reduced under rotoevaporation to provide a yellow liquid, which is purified by flash column chromatography on silica gel using DCM and 1:20 MeOH/DCM gradient to provide the product in 65% yield.

Preparation of Menaquinol Compounds I:

The preparation of the diesters or mono-esters of the compound of the Formula I may be performed using standard acetylation of quinones known in the art. For example, the quinone may be treated with a symmetrical anhydride, where R$^a$ and R$^b$ are the same group, or with an asymmetrical anhydride, where R$^a$ and R$^b$ are different groups. In one embodiment of the symmetrical or asymmetrical anhydride, the acyl group R$^a$—C(O)— is selected from the group consisting of:

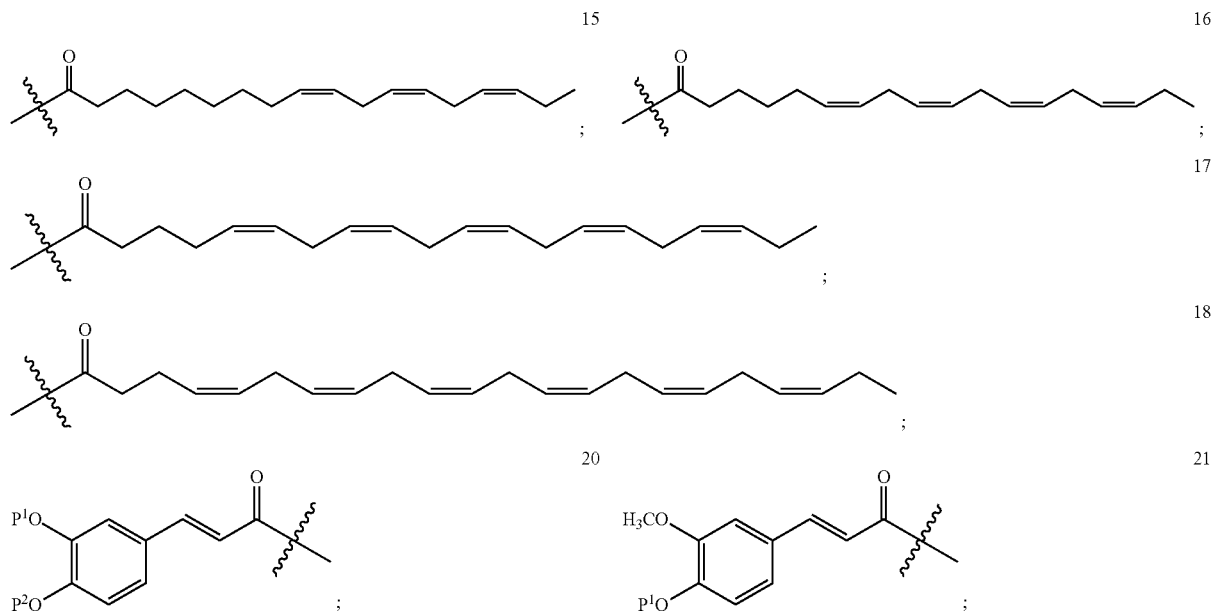

-continued

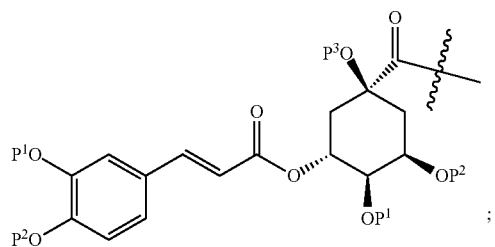
22

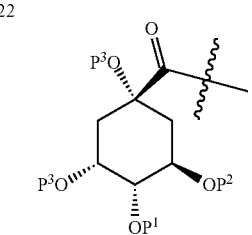
23

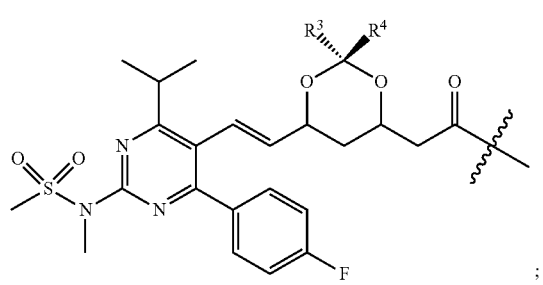
24

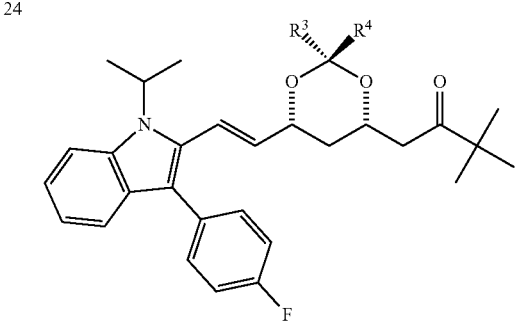
25

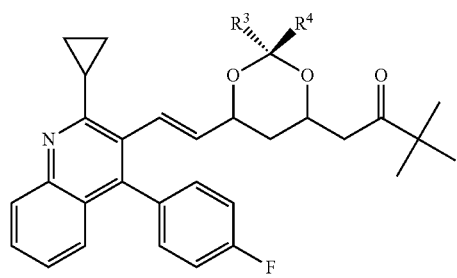
26

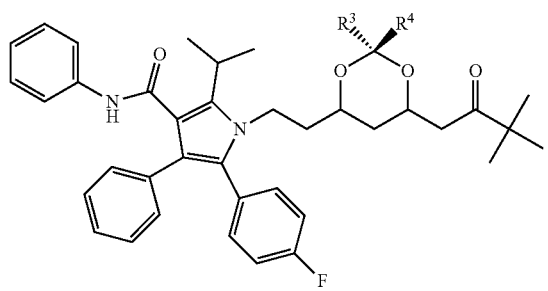
27
; and

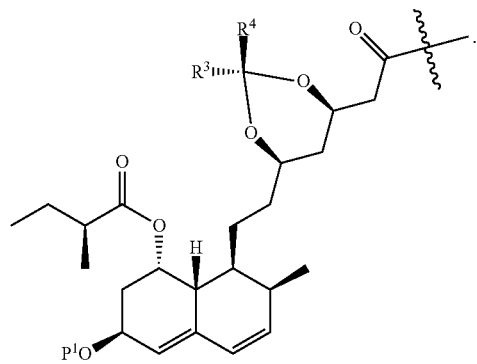
28
.

and $R^b$ may be the same as $R^a$ or $R^b$ may be selected from —CH$_3$ or —CH$_2$CH$_3$; wherein P$^1$ and P$^2$ are each independently a protecting group such as —CH$_2$C6H$_5$, -THP (tetrahydropyranyl) or P$^1$ and P$^2$ together with the oxygen to which they are attached form a cyclic acetonide, benzyl acetal or p-methoxy-benzyl acetal; P$^3$ is a hydroxyl protecting group such as -THP, acetyl, benzoyl, β-methoxyethoxymethyl ether (MEM), dimethoxytrityl, methoxymethyl ether (MOM), p-methoxybenzyl ether (PMB), methylthiomethyl ether, pivaloyl (Piv) and trityl (Tr); and each R$^3$ and R$^4$ is independently H, —CH$_3$, —CH$_2$CH$_3$ and —CH$_2$C6H$_5$; and the acetylation may be performed with the addition of a base such as Cs$_2$CO$_3$, CsHCO$_3$, LiCO$_3$, Na$_2$CO$_3$, K$_2$CO$_3$, KHCO$_3$, NaOAc and NaHCO$_3$. The acylation may be performed in a solvent such as THF, Me-THF, toluene and ethyl acetate.

In another embodiment, the preparation of the diesters or mono-esters of menaquinol-7 of Formula I (R$^1$=R$^2$=H) may be performed using standard acetylation of quinones using an acid halide as known in the art, where the halide is —Cl, —Br or —I along with a base selected from the group consisting of Cs$_2$CO$_3$, CsHCO$_3$, CsOH, LiCO$_3$, Na$_2$CO$_3$, K$_2$CO$_3$, KHCO$_3$, NaOAc, NaHCO$_3$, or an organic amine base as disclosed herein. For example, in one embodiment of the symmetrical or unsymmetrical anhydride, the acyl group R$^a$—C(O)— is selected from the group consisting of the above residues including 15, 16, 17, 18, 20, 21, 22, 2, 24, 2, 26, 27 and 28.

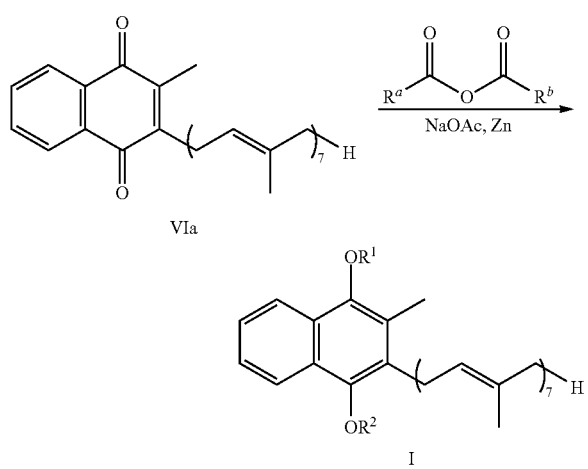

Preparation of a Menaquinol I($R^1$ and $R^2$ are as Defined Herein):

Menaquinone-7 (VIa, 1.00 g, 1.54 mmol), the symmetrical anhydride where $R^a$ and $R^b$ are both the acyl group 15 (1.67 g, 3.08 mmol, MW=544 g/ml). NaOAc (0.154 g, 1.88 mmol) and Zn powder (0.35 g, 5.44 mmol) are added together in a 50 mL RBF equipped with a stirr bar and heated to about 140° C. for about 1 hour. The resulting mixture was cooled to RT and THF (45 mL) is added. Et$_2$N (20 mL) is added and the resulting mixture is stirred for another 30 minutes, and then heptane (60 mL) is added. The resulting mixture is filtered using a buchner funnel and filter paper, and the filtered cake is washed with heptane (2×15 mL). The solvents in the combined filtrate is removed under rotoevaporation at a water bath of about 35° C. and the resulting oil is purified by flash column chromatography (heptane:EtOAc in gradient) to provide 41.9 g (about 50%) yield of the menaquinol I, where $R^1$ and $R^2$ are both the acyl group 15.

Preparation of a Menaquinol I($R$=$R^2$=H):

Menaquinone-7 (VIa, 1.00 g, 1.54 mmol), the symmetrical anhydride where $R^a$ and $R^b$ are both the acyl group 15 (1.67 g, 3.08 mmol, MW=544 g/ml). NaOAc (0.154 g, 1.88 mmol) and Zn powder (0.35 g, 5.44 mmol) are added together in a 50 mL RBF equipped with a stir bar and heated to about 140° C. for about 1 hour. The resulting mixture was cooled to RT and THF (45 mL) is added. Et$_2$N (20 mL) is added and the resulting mixture is stirred for another 30 minutes, and then heptane (60 mL) is added. The resulting mixture is filtered using a buchner funnel and filter paper, and the filtered cake is washed with heptane (2×15 mL). The solvents in the combined filtrate is removed under rotoevaporation at a water bath of about 35° C. and the resulting oil is purified by flash column chromatography (heptane:EtOAc in gradient) to provide 41.9 g (about 50%) yield of the menaquinol I, where $R^1$ and $R^2$ are both the acyl group 15.

Administration of the Compounds of the Present Application (the Disclosed Compounds) in Subjects at Risk for Development of Calciphylaxis:

This example describes the administration of the compounds of the present application to subjects at risk for development of calciphylaxis, but who have not yet developed the characteristic skin lesions of calciphylaxis. Risk factors to be considered include, but are not limited to, diabetes mellitus, obesity, hemodialysis, and prior treatment with warfarin (Nigwekar et al. (2016) "A Nationally Representative Study of Calcific Uremic Arteriolopathy Risk Factors," J. AM. SOC. NEPHROL. 27(11):3421-9)). The administration of these compounds can result in protection of the subjects from skin lesions and a change in certain biomarker levels indicative of the prevention of the development of calciphylaxis.

Subjects at risk of development of calciphylaxis orally receive a selected compound of the present application at 5 mg, 10 mg, 25 mg or 50 mg once daily for at least 2 weeks, 4 weeks, 6 weeks, 8 weeks, 3 months, 6 months, 1 year, or indefinitely. The dosage form is a 5 mg, 10 mg or 25 mg soft-gel capsule. Two 25 mg capsules are be administered once daily to the 50 mg dosage cohort. It should be noted that not all subjects with elevated risk factors for calciphylaxis will develop the characteristic skin lesions of calciphylaxis. The intent of treating with the compound of the present application proactively (prior to a clinical diagnosis of calciphylaxis) is the prevention of lesion appearance. Thus, a drop in frequency of, or elimination of lesion appearances is contemplated to be a successful treatment.

Several biomarkers can be assessed to determine the efficacy of the compound to be administered at the three dose levels. Exemplary biomarkers include PIVKA-II; uncarboxylated and total Matrix Gla Protein (MGP); uncarboxylated, carboxylated and total osteocalcin protein; uncarboxylated, carboxylated and total Protein C, osteoprotegerin, Fetuin A and hs-CRP. Blood samples are obtained to measure the biomarkers according to the following schedule. Blood sampling can occur during treatment on a weekly or monthly basis. It is contemplated that administration of the disclosed compounds will result in (i) an increase in PIVKA-II, which is indicative of slowing the progression of, arresting, or reversing, calciphylaxis, (ii) a decrease in uncarboxylated MGP, uncarboxylated osteocalcin, and/or uncarboxylated Protein C, which is indicative of slowing the progression of, arresting, or reversing calciphylaxis. Further, pulse wave velocity (PWV) can be measured to assess arterial compliance. Improved vascular compliance will be indicative of slowing the progression of, arresting, or reversing calciphylaxis.

Administration of the Disclosed Compounds of the Application in Subjects Diagnosed with Calciphylaxis:

This example describes the administration of the disclosed compounds to subjects diagnosed with calciphylaxis. Typical symptoms include presentation of characteristic painful skin lesions (Nigwekar et al. (2015) Calciphylaxis: Risk Factors, Diagnosis, and Treatment. Am. J. Kidney Dis. 66:133-46). Definitive diagnosis of calciphylaxis is achieved via skin biopsy. Further conditions need to be considered for correct diagnosis.

Subjects diagnosed with calciphylaxis orally receive the disclosed compound at 5 mg, 10 mg, 25 mg or 50 mg once daily for at least 2 weeks, 4 weeks, 6 weeks, 8 weeks, 3 months, 6 months, 1 year, or indefinitely. The dosage form is a 5 mg, 10 mg or 25 mg soft-gel capsule. Two 25 mg capsules are administered once daily to the 50 mg dosage cohort.

The arrest of, or decreases in lesion size and frequency is contemplated to be an indication of successful treatment. The administration of the disclosed compounds according to the foregoing will result in the arrest of, or decrease in lesion size and frequency. Additionally, because calciphylaxis has a considerable mortality risk, increased overall survival time of diagnosed subjects will be an indication of treatment success. Furthermore, the administration of the disclosed compounds according to the foregoing will result in an increased overall survival time of diagnosed subjects.

Administration of the Disclosed Compounds in Subjects with End Stage Renal Disease (ESRD) to Reverse or Slow the Progression of Tissue Calcification:

This example describes the administration of the disclosed compounds to a subject with ESRD and on stable hemodialysis. The administration of the disclosed compounds will result in a change in aortic compliance (via plethysmography), vascular calcification and certain biomarker levels indicative of slowing the progression of, arresting, or reversing tissue calcification.

ESRD subjects on stable hemodialysis orally receive the disclosed compounds at 5 mg, 10 mg, 25 mg or 50 mg once daily for least 2 weeks, 4 weeks, 6 weeks, 8 weeks, 3 months, 6 months, 1 year, or indefinitely. The dosage form is a 5 mg, 10 mg or 25 mg soft-gel capsule. Two 25 mg capsules are administered once daily to the 50 mg dosage cohort.

A 50 y.o., 65 kg male patient diagnosed with the typical symptoms associated with moderate calciphylaxis is treated with 10 mg of the compound of the formula I wherein m is 7, $R^1$ the compound of the formula 24, $R^2$ is H and $R^3$ and $R^4$ are both —$CH_3$, for a period of 8 weeks. After the treatment period, the patient is admitted and evaluated. The patient was found to have a significant change in the examined biomarker levels suggesting about a 10% reduction in vascular calcification, and is also shown to have a 10% reduction in tissue calcification.

A 65 y.o., 45 kg female patient diagnosed with the typical symptoms associated with moderate calciphylaxis is treated with 10 mg of the compound of the formula I wherein m is 7, $R^1$ the compound of the formula 25, $R^2$ is H and $R^3$ and $R^4$ are both —$CH_3$, for a period of 10 weeks. After the treatment period, the patient is admitted and evaluated. The patient was found to have a significant change in the examined biomarker levels suggesting about a 20% reduction in vascular calcification, and is also shown to have a 15% reduction in tissue calcification.

A 55 y.o., 70 kg male patient diagnosed with the typical symptoms associated with moderate calciphylaxis is treated with 20 mg of the compound of the formula I wherein m is 7, $R^1$ the compound of the formula 26, $R^2$ is H and $R^3$ and $R^4$ are both —$CH_3$, for a period of 3 months. After the treatment period, the patient is admitted and evaluated. The patient was found to have a significant change in the examined biomarker levels suggesting about a 25% reduction in vascular calcification, and is also shown to have a 20% reduction in tissue calcification.

Coronary arterial calcium scores (CAC) are used to estimate the extent of calcification of thoracic arteries. A high CAC score is indicative of calcification, and treatment has the aim of arresting the long term increase in CAC score, or reversing it, or slowing the rate of increase.

Aortic plethysmography also is used to measure arterial compliance, which decreases as calcification increases. Pulse wave velocity (PWV) also is measured to assess arterial compliance. The foregoing measures are useful in estimating the utility of treatments intended to prevent, slow the progression of, arrest or reverse vascular calcification. These measurements are used pre- and post-treatment with the disclosed compounds to assess treatment value.

Further, several biomarkers are assessed to determine the efficacy of the disclosed compounds at the three dose levels. Exemplary biomarkers include PIVKA-II; uncarboxylated and total Matrix Gla Protein (MGP); uncarboxylated, carboxylated and total osteocalcin protein; uncarboxylated, carboxylated and total Protein C, and hs-CRP. Blood samples are obtained to measure the biomarkers, most conveniently during patient visits for hemodialysis.

The administration of the disclosed compounds can result in (i) an increase in PIVKA-II, which is indicative of slowing the progression of, arresting or reversing tissue calcification, (ii) a decrease in uncarboxylated MGP, uncarboxylated osteocalcin, and/or uncarboxylated Protein C, which is indicative of slowing the progression of, arresting or reversing tissue calcification, and/or (iii) a decrease in hs-CRP, which is indicative of slowing the progression of, arresting or reversing tissue calcification and/or reduced inflammation. Following the daily administration of 5 mg, 10 mg, 25 mg or 50 mg of the disclosed compounds and compositions, at least one of PIVKA-II, under-carboxylated Matrix Gla Protein (MGP), under-carboxylated osteocalcin protein, will show a change indicative of slowing the progression of, arresting or reversing tissue calcification.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

References: 1) Rachel M. Holden et al. Vitamins K and D Status in Stages 3-5 Chronic Kidney Disease; *Clin J Am Soc Nephrol* 5: 590-597, 2010. 2) Pilkey, R. M. M D et al. Subclinical Vitamin K Deficiency in Hemodialysis Patients Am J Kidney Dis 49:432-439, 2007. 3) Westhofen P et al. Human vitamin K 2,3-epoxide reductase complex subunit 1-like 1 (VKORC1L1) mediates vitamin K-dependent intracellular antioxidant function. J Biol Chem 2011; 286: 15085-94. 4) Caspers, M. et al., Two enzymes catalyze vitamin K 2,3-epoxide reductase activity in mouse: VKORC1 is highly expressed in exocrine tissues while VKORC1L1 is highly expressed in brain. Thrombosis Research 135:977-983, 2015. 5) Himmelfarb, J. et al., Plasma protein thiol oxidation and carbonyl formation in chronic renal failure. *Kidney International*, Vol. 58: 2571-2578 2000. 6) Price, P. A. et al., Discovery of a High Molecular Weight Complex of Calcium, Phosphate, Fetuin, and Matrix-Carboxyglutamic Acid Protein in the Serum of Etidronate-treated Rats. Journal Biol Chem. 277 (6): 3926-3934, 2002. 7) Pasch, A. et al. Nanoparticle-Based Test Measures Overall Propensity for Calcification in Serum J Am Soc Nephrol 23: 1744-1752, 2012. 8) Nigwekar, S. U. et al. Vitamin K-Dependent Carboxylation of Matrix Gla Protein Influences the Risk of Calciphylaxis. J Am Soc Nephrol 28: 1717-1722, 2017.

What is claimed is:

1. A menaquinol compound of the Formula I:

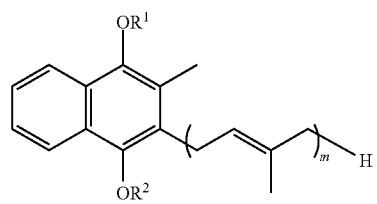

wherein:

m is 7, 8, 9 or 10;

$R^1$ and $R^2$ are both the residue 15;
$R^1$ and $R^2$ are both the residue 16;
$R^1$ and $R^2$ are both the residue 17;
$R^1$ and $R^2$ are both the residue 18;
$R^1$ and $R^2$ are both the residue 20;
$R^1$ and $R^2$ are both the residue 21;
$R^1$ and $R^2$ are both the residue 22;
$R^1$ and $R^2$ are both the residue 23;
$R^1$ and $R^2$ are both the residue 24;
$R^1$ and $R^2$ are both the residue 25;
$R^1$ and $R^2$ are both the residue 26;
$R^1$ and $R^2$ are both the residue 27;
$R^1$ and $R^2$ are both the residue 28;
$R^1$ is H and $R^2$ is the residue 15; $R^2$ is H and $R^1$ is the residue 15;
$R^1$ is H and $R^2$ is the residue 16; $R^2$ is H and $R^1$ is the residue 16;
$R^1$ is H and $R^2$ is the residue 17; $R^2$ is H and $R^1$ is the residue 17;
$R^1$ is H and $R^2$ is the residue 18; $R^2$ is H and $R^1$ is the residue 18;
$R^1$ is H and $R^2$ is the residue 20; $R^2$ is H and $R^1$ is the residue 20;
$R^1$ is H and $R^2$ is the residue 21; $R^2$ is H and $R^1$ is the residue 21;
$R^1$ is H and $R^2$ is the residue 22; $R^2$ is H and $R^1$ is the residue 22;
$R^1$ is H and $R^2$ is the residue 23; $R^2$ is H and $R^1$ is the residue 23;
$R^1$ is H and $R^2$ is the residue 24; $R^2$ is H and $R^1$ is the residue 24;
$R^1$ is H and $R^2$ is the residue 25; $R^2$ is H and $R^1$ is the residue 25;
$R^1$ is H and $R^2$ is the residue 26; $R^2$ is H and $R^1$ is the residue 26;
$R^1$ is H and $R^2$ is the residue 27; $R^2$ is H and $R^1$ is the residue 27; and
$R^1$ is H and $R^2$ is the residue 28; $R^2$ is H and $R^1$ is the residue 28;

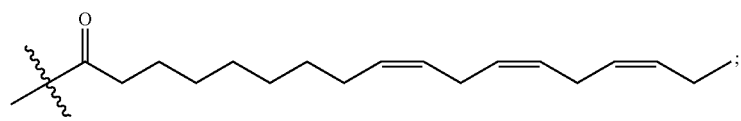
15

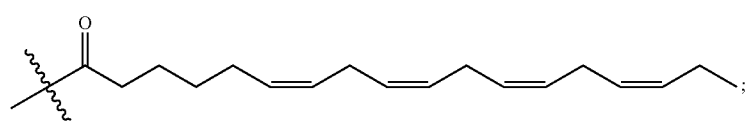
16

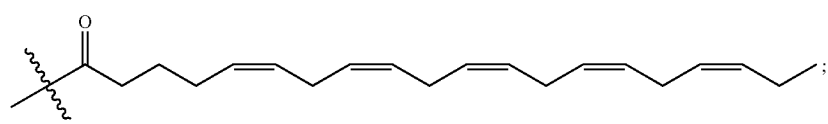
17

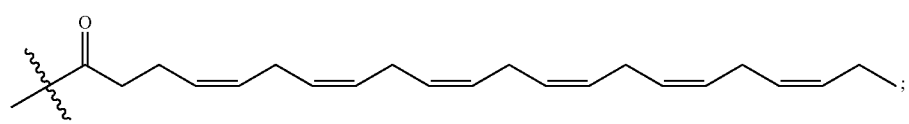
18

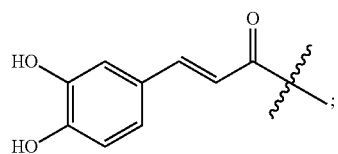
20

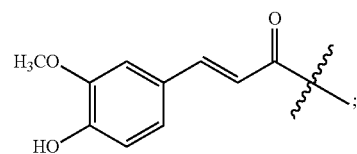
21

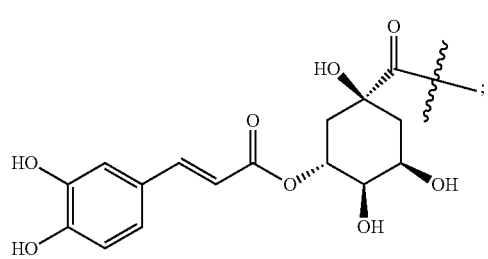
22

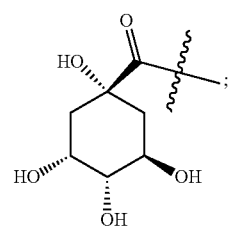
23

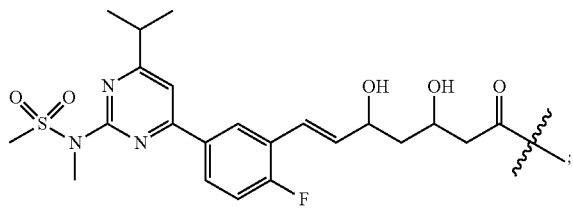

24

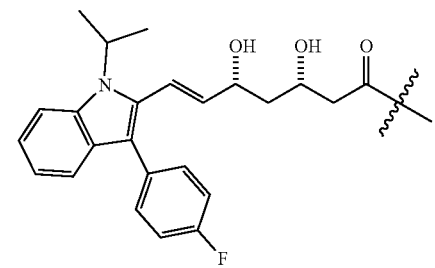

25

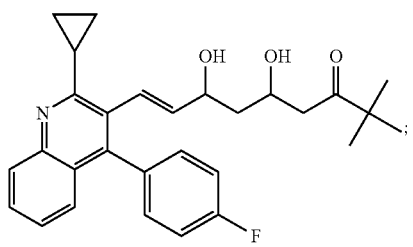

26

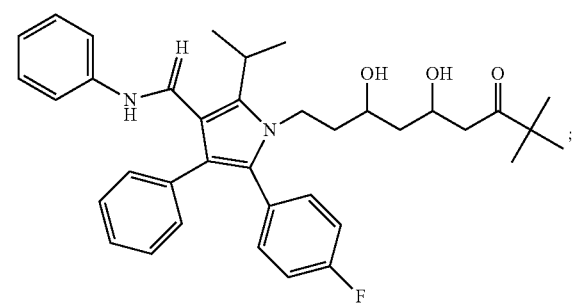

27 and

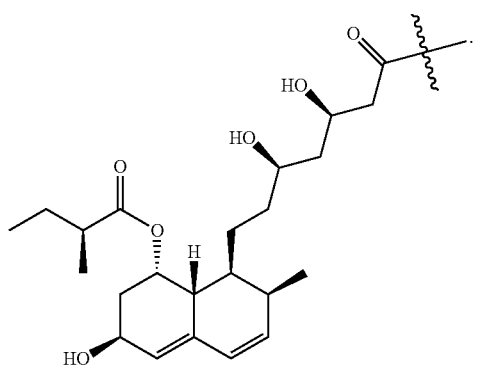

28

2. The compound of claim 1 of the Formula I, wherein:
$R^1$ and $R^2$ are both the residue 15;
$R^1$ and $R^2$ are both the residue 16;
$R^1$ and $R^2$ are both the residue 17;
$R^1$ and $R^2$ are both the residue 18;
$R^1$ and $R^2$ are both the residue 20;
$R^1$ and $R^2$ are both the residue 21;
$R^1$ and $R^2$ are both the residue 22;
$R^1$ and $R^2$ are both the residue 23;
$R^1$ and $R^2$ are both the residue 24;
$R^1$ and $R^2$ are both the residue 25;
$R^1$ and $R^2$ are both the residue 26;
$R^1$ and $R^2$ are both the residue 27; and
$R^1$ and $R^2$ are both the residue 28.

3. The compound of claim 1 of the Formula I, wherein:
$R^1$ is H and $R^2$ is the residue 15; $R^2$ is H and $R^1$ is the residue 15;
$R^1$ is H and $R^2$ is the residue 16; $R^2$ is H and $R^1$ is the residue 16;
$R^1$ is H and $R^2$ is the residue 17; $R^2$ is H and $R^1$ is the residue 17;
$R^1$ is H and $R^2$ is the residue 18; $R^2$ is H and $R^1$ is the residue 18;
$R^1$ is H and $R^2$ is the residue 20; $R^2$ is H and $R^1$ is the residue 20;
$R^1$ is H and $R^2$ is the residue 21; $R^2$ is H and $R^1$ is the residue 21;
$R^1$ is H and $R^2$ is the residue 22; $R^2$ is H and $R^1$ is the residue 22;
$R^1$ is H and $R^2$ is the residue 23; $R^2$ is H and $R^1$ is the residue 23;
$R^1$ is H and $R^2$ is the residue 24; $R^2$ is H and $R^1$ is the residue 24;
$R^1$ is H and $R^2$ is the residue 25; $R^2$ is H and $R^1$ is the residue 25;
$R^1$ is H and $R^2$ is the residue 26; $R^2$ is H and $R^1$ is the residue 26;
$R^1$ is H and $R^2$ is the residue 27; $R^2$ is H and $R^1$ is the residue 27; and
$R^1$ is H and $R^2$ is the residue 28; $R^2$ is H and $R^1$ is the residue 28.

4. The menaquinol compound of the Formula I of claim 1, wherein
m is 7, 8, 9 or 10;
$R^1$ is H and $R^2$ is the acyl residue of caffeic acid 20: or
$R^2$ is H and $R^1$ is the acyl residue of caffeic acid 20;

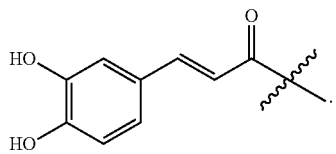

20

5. The menaquinol compound of the Formula I of claim 1, wherein
m is 7, 8, 9 or 10;
$R^1$ is H and $R^2$ is or the acyl residue of ferulic acid 21; or
$R^2$ is H and $R^1$ is the acyl residue of ferulic acid 21;

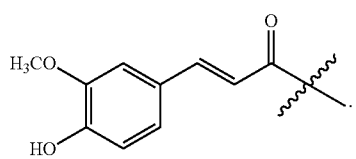

21

6. The menaquinol compound of the Formula I of claim 1, wherein
m is 7, 8, 9 or 10;
$R^1$ is H and $R^2$ is the acyl residue of chlorogenic acid 22; or
$R^2$ is H and $R^1$ is the acyl residue of chlorogenic acid 22;

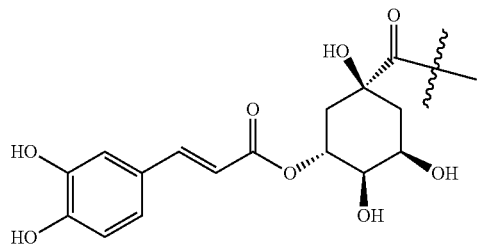

22

7. The menaquinol compound of the Formula I of claim 1, wherein
m is 7, 8, 9 or 10;
$R^1$ is H and $R^2$ is the acyl residue of quinic acid 23; or
$R^2$ is H and $R^1$ is the acyl residue of quinic acid 23;

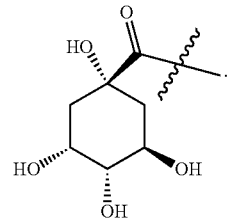

23

* * * * *

UNITED STATES PATENT AND TRADEMARK OFFICE
CERTIFICATE OF CORRECTION

PATENT NO. : 10,822,295 B2
APPLICATION NO. : 16/563099
DATED : November 3, 2020
INVENTOR(S) : Keith E. Drouet, James A. Tumlin and John M. Rudey It is certified that error appears in the above-identified patent and that said Letters Patent is hereby corrected as shown below:

On the Title Page

Inventor James A. Tumlin's city and state should read, in its entirety:
James A. Tumlin, Buford, GA Add third inventor as follows:
John M. Rudey, New York, NY Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*